(12) United States Patent
Tanaka

(10) Patent No.: US 7,372,062 B2
(45) Date of Patent: May 13, 2008

(54) DEFECT INSPECTION DEVICE AND SUBSTRATE MANUFACTURING SYSTEM USING THE SAME

(75) Inventor: Toshihiko Tanaka, Yokohama (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/584,724

(22) Filed: Oct. 20, 2006

(65) Prior Publication Data

US 2007/0103893 A1    May 10, 2007

Related U.S. Application Data

(63) Continuation of application No. PCT/JP2005/007553, filed on Apr. 20, 2005.

(30) Foreign Application Priority Data

Apr. 22, 2004   (JP) .......................... P2004-126767

(51) Int. Cl.
*G01N 21/88* (2006.01)
(52) U.S. Cl. .................. 250/559.45; 250/559.4; 250/559.44; 356/237.1; 356/237.2; 356/237.3
(58) Field of Classification Search ............ 250/559.4, 250/559.45–559.49; 356/237.1–237.5
See application file for complete search history.

(56) References Cited

U.S. PATENT DOCUMENTS

| | | | |
|---|---|---|---|
| 6,407,818 B1 * | 6/2002 | Whitehouse ................. | 356/627 |
| 6,501,545 B2 * | 12/2002 | Komuro et al. ............. | 356/237.2 |
| 6,515,745 B2 * | 2/2003 | Vurens et al. ............... | 356/369 |
| 6,816,250 B1 * | 11/2004 | Shuster et al. ............. | 356/237.2 |
| 6,950,196 B2 * | 9/2005 | Fielden et al. .............. | 356/630 |
| 6,954,012 B2 * | 10/2005 | Lau ........................... | 310/68 B |
| 6,954,268 B2 * | 10/2005 | Naiki et al. ............... | 356/237.2 |
| 7,123,357 B2 * | 10/2006 | Meeks ....................... | 356/237.3 |
| 2002/0017620 A1 * | 2/2002 | Oomori et al. .......... | 250/559.4 |
| 2002/0024659 A1 * | 2/2002 | Tanaka ..................... | 356/237.2 |
| 2004/0174518 A1 * | 9/2004 | Naiki et al. .............. | 356/237.2 |
| 2005/0116187 A1 * | 6/2005 | Uda et al. .............. | 250/559.45 |

FOREIGN PATENT DOCUMENTS

| | | |
|---|---|---|
| JP | 63-143831 A | 6/1988 |
| JP | 63-205775 A | 8/1988 |
| JP | 3-102845 A | 4/1991 |

(Continued)

OTHER PUBLICATIONS

English Abstract of JP 2003-028805 (cited on Applicant's IDS dated Oct. 20, 2006).*

(Continued)

*Primary Examiner*—Davienne Monbleau
(74) *Attorney, Agent, or Firm*—Frishauf, Holtz, Goodman & Chick, P.C.

(57) ABSTRACT

A defect inspection device which inspects for surface defects in substrates, and which includes an illumination section that irradiates the substrate with illumination light having a variable incident angle, and a light-receiving section that receives light from the substrate irradiated with illumination light from the illumination section with a variable detection angle. The light-receiving section receives diffracted light emitted in substantially the same direction as the direction of incidence of the illumination light from the illumination section.

12 Claims, 10 Drawing Sheets

FOREIGN PATENT DOCUMENTS

| | | |
|---|---|---|
| JP | 07-027709 A | 1/1995 |
| JP | 7-198620 A | 8/1995 |
| JP | 8-247957 A | 9/1996 |
| JP | 09-061365 A | 3/1997 |
| JP | 2003-28805 A | 1/2003 |
| JP | 2003-344295 A | 12/2003 |
| WO | WO 01/71323 A1 | 9/2001 |

OTHER PUBLICATIONS

English Abstract of JP 63-205775 (cited on Applicant's IDS dated Oct. 20, 2006).*

English Abstract of JP 08-247957 (cited on Applicant's IDS dated Oct. 20, 2006).*

English translation of JP 2003-344295 (cited on Applicant's IDS dated Oct. 20, 2006).*

* cited by examiner

US 7,372,062 B2

DEFECT INSPECTION DEVICE AND SUBSTRATE MANUFACTURING SYSTEM USING THE SAME

CROSS-REFERENCE TO RELATED APPLICATION

This is a Continuation Application of International Application No. PCT/JP2005/007553, filed Apr. 20, 2005, which claims priority to Japanese Patent Application No. 2004-126767, filed Apr. 22, 2004. The contents of the aforementioned applications are incorporated herein by reference.

BACKGROUND OF THE INVENTION

1. Field of the Invention

The present invention relates to a defect inspection device and a substrate manufacturing system using the same. For example, the invention relates to a defect inspection device that inspects surface defects in a substrate, such as a semiconductor wafer and a liquid crystal substrate, and a substrate manufacturing system using the defect inspection device.

2. Description of Related Art

Semiconductor wafers and liquid crystal substrates are generally manufactured by performing a photolithography process to a substrate of silicon, glass, and the like. During this photolithography process, if there is film unevenness or dust and the like sticking to a resist applied over the substrate surface, this can cause poor line-width in the pattern after etching, pinholes in the pattern, and other defects.

Accordingly, an exhaustive inspection is made to determine the existence of such defects in a manufacturing step of the substrate prior to etching. While this inspection is often performed by visual observation by an operator, discrepancies in the operator's judgment and effects of dust emanating from the operator himself in a clean room cannot be ignored, and consequently there are proposals for methods that use a defect inspection device including a determination function.

For example, Japanese Unexamined Patent Application, First Publication No. H09-61365 discloses a device including an illumination section that illuminates the surface of a specimen at an angle $\theta_0$, a first image-capturing section for capturing regular reflected light that is arranged at a position of angle $\theta_0$, a second image-capturing section for capturing diffracted light that is arranged at a perpendicular position, and a third image-capturing section for capturing scattered light that is arranged at a position of angle $\theta_1$.

In addition, Japanese Unexamined Patent Application, First Publication No. H07-27709 discloses a device including an image-capturing section and two bundles of fibers that lead illumination light, enabling incident angles $\theta_1$ and $\theta_2$ and incident angles $\psi_1$ and $\psi_2$ to be set freely.

SUMMARY OF THE INVENTION

A defect inspection device of the invention includes an illumination section that irradiates a specimen with illumination light having a variable incident angle, and a light-receiving section that receives light from the specimen irradiated with illumination light from the illumination section with a variable detection angle, wherein the illumination section and the light-receiving section rotates around a rotational axis that includes an intersection point at which an optical axis of the illumination section, an optical axis of the light-receiving section, and a surface of the specimen intersect, and the light-receiving section receives the light emitted in substantially the same direction as the direction of incidence of the illumination light from the illumination section.

DETAILED DESCRIPTION OF THE INVENTION

Figure 1:
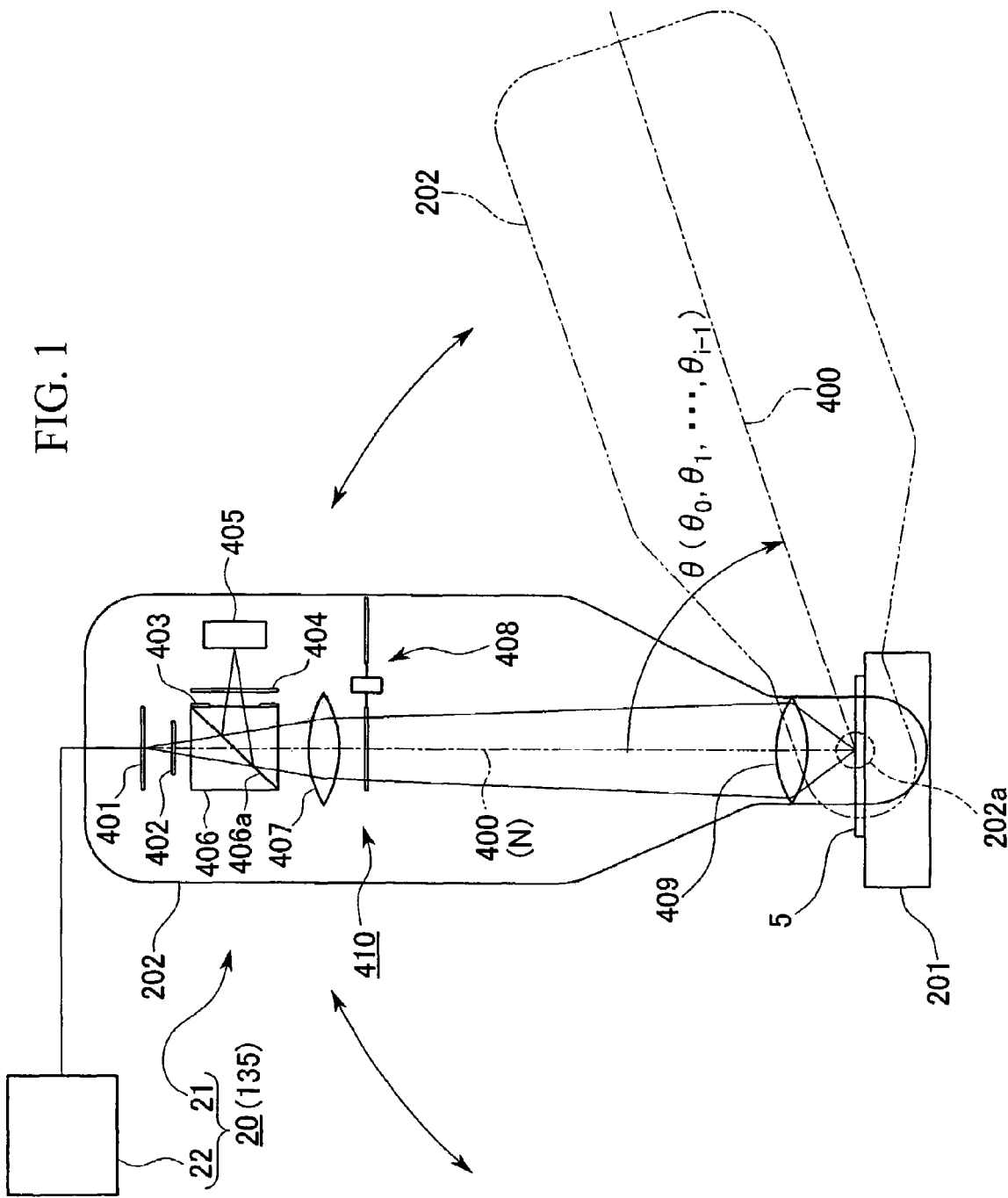
FIG. 1 is a conceptual diagram for explanation of a schematic configuration of a defect inspection device according to an embodiment of the invention.

Embodiments of the invention will be described below with reference to the accompanying drawings. In all the drawings, same and corresponding parts are designated with same reference numerals and are not repetitiously explained, even when their arrangements differ.

First Embodiment

A defect inspection device according to a first embodiment of the invention will be explained.

Figure 2A:
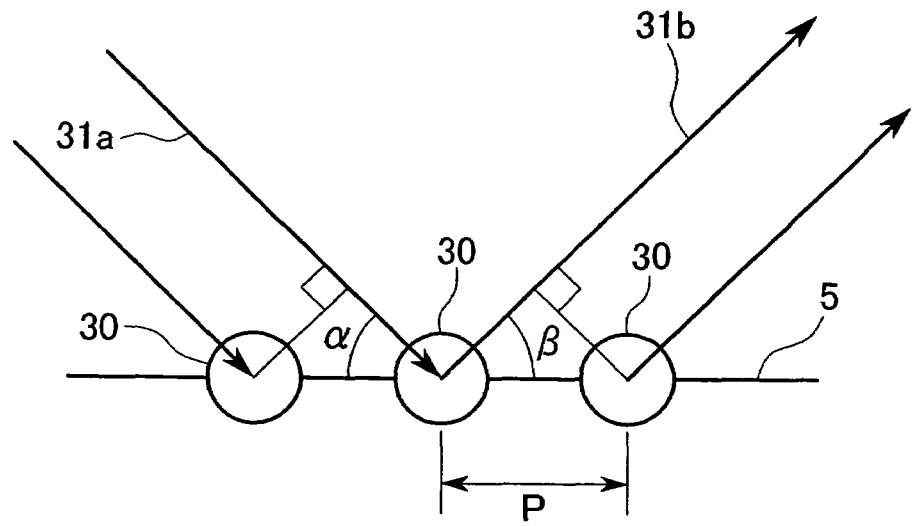
FIG. 2A is a principle diagram for explanation of light refracted using a regular pattern.
Figure 2B:
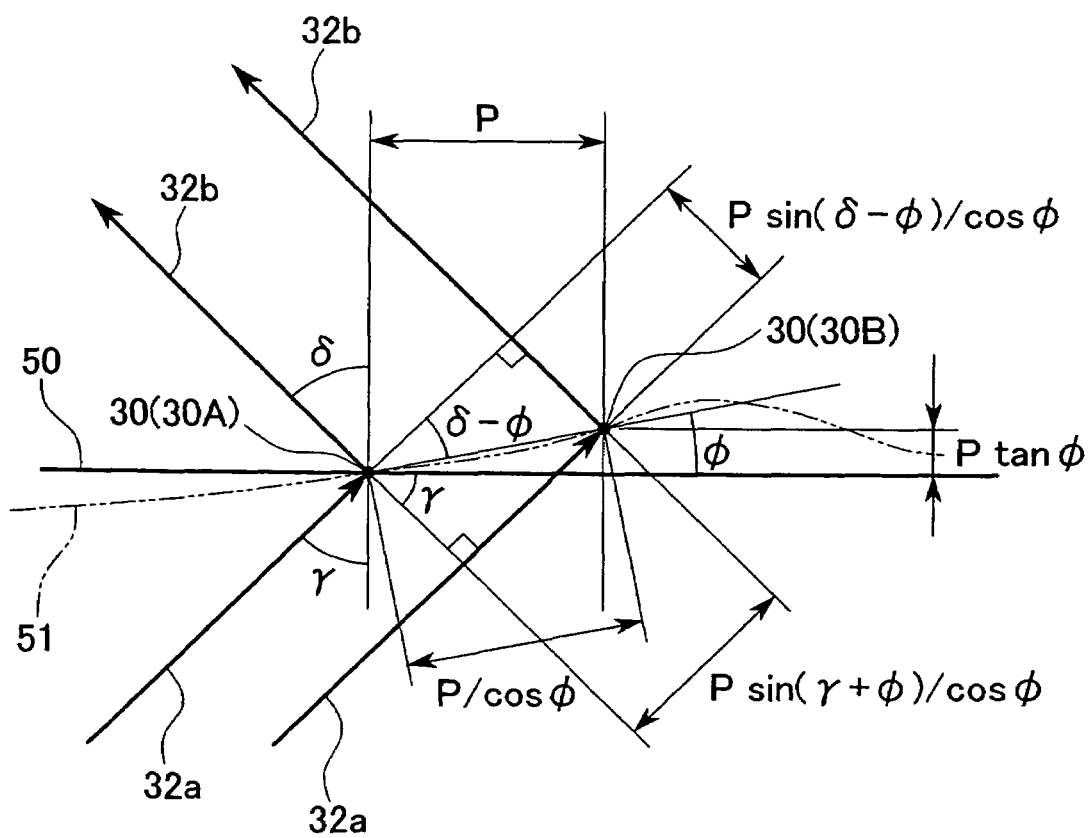
FIG. 2B is a schematic optical path diagram representing the relationship between light that is incident on a permeable face and refracted light for explanation of Bragg's law.
Figure 3:
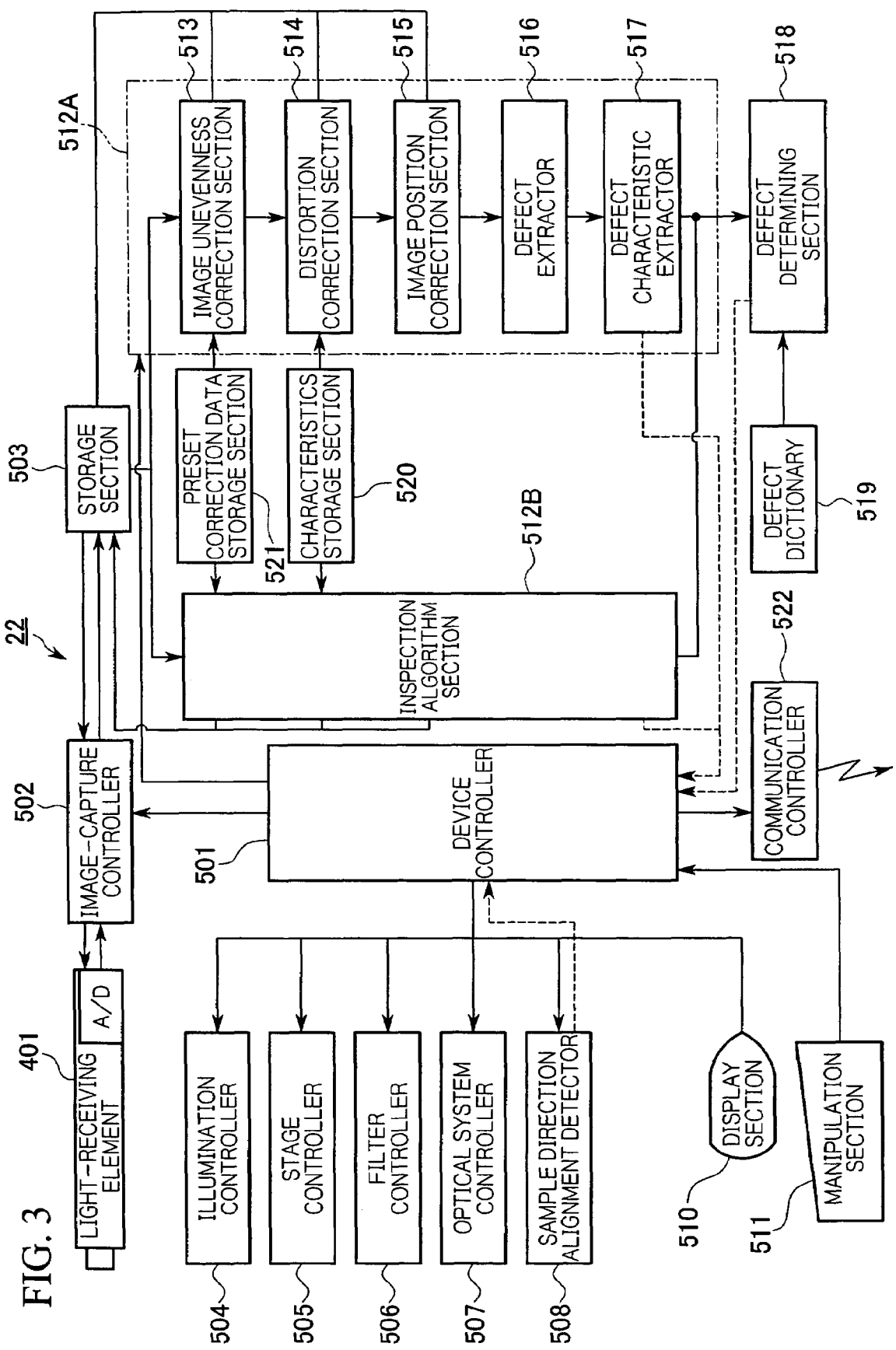
FIG. 3 is a functional block diagram for explanation of a schematic configuration of a controller/processor of the defect inspection device according to a first embodiment of the invention.

FIG. 1 is a conceptual diagram for explanation of a schematic configuration of a defect inspection device according to an embodiment of the invention. FIG. 2A is a principle diagram for explanation of light refracted using a regular pattern. FIG. 2B is a schematic optical path diagram representing the relationship between light that is incident on a permeable face and refracted light for explanation of Bragg's law. FIG. 3 is a functional block diagram for explanation of a schematic configuration of a controller/processor of the defect inspection device according to a first embodiment of the invention.

As shown in FIG. 1, a defect inspection device 20 of this embodiment includes an illumination light-receiving section 21 and a controller/processor 22 that performs various controls and processes images.

The illumination light-receiving section 21 includes an optical holding section 202, and an illumination/light-receiving optical system 410 that includes an illumination optical system (illumination section) and a light-receiving optical system (light-receiving section) which are held together in the optical holding section 202.

The optical holding section 202 is a casing member that is provided above a stage 201 that movably transports a specimen 5 attached by a suitable attaching mechanism, and is movably supported with respect to an inspection position on the stage 201 by a holding section moving mechanism 202a. The inspection position on the stage 201 is secured on a top face of the specimen 5 arranged on the stage 201 in a vertical direction, and in the moving direction of the specimen 5 in a horizontal direction, and arranged in a straight line or a straight strip extending in a direction that intersects with the moving direction (the direction perpendicular to the paper in FIG. 1).

The holding section moving mechanism 202a includes a rotating shaft, a motor (not shown) that provides rotation drive power around the rotating shaft, and such like, the angle of rotation being controlled by a optical system movement controller 509 described below. Here, the rotating shaft includes the intersection point of the optical axis of the illumination/light-receiving optical system and the surface of the specimen (a substrate including a pattern regularly arranged on a surface of a semiconductor, a liquid crystal, etc.), and is parallel to the longitudinal direction of the line shape of an illumination section described below.

The illumination/light-receiving optical system 410 includes an illumination optical system that irradiates a band of illumination light onto an inspection position and a light-receiving optical system that receives light emitted from the inspection position, these being integrated such that they are partial coaxial and share the optical path. An optical axis 400 is an optical axis of this shared part.

The optical holding section 202 depicted by a solid line in FIG. 1, represents a case when the optical axis 400 of the illumination/light-receiving optical system 410 overlaps the normal line N of the specimen 5, i.e., when the incident angle of the illumination light against the specimen 5 is 0°. The optical holding section 202 depicted by a dashed two-dotted line in FIG. 1 represents a case when the optical axis 400 is rotated clockwise as viewed in FIG. 1 by an angle θ with respect to the normal line N of the specimen 5, i.e., when the incident angle of the illumination light is θ.

The illumination/light-receiving optical system 410 basically includes a light source 405, a scattering plate 404, a half mirror 406, a condensing lens 407, a lens 409, and a light-receiving element 401.

The light source 405 irradiates the specimen 5 with a band of uniform illumination light. For example, a plurality of halogen lamps or metal halide lamps can be aligned to form the light source 405, and light from them can be transmitted by optical fibers and the like. In this case, to increase the utilization efficiency of the light, it is important that the exit angle range of the light is within the NA range of the condensing lens 407 explained below; when such a design is difficult, the light utilization efficiency can be increased by providing a mirror and the like behind the light source.

In this embodiment, although not shown in the diagrams, a plurality of white LEDs are arranged to provide a band-like illumination parallel to a specimen such as a substrate. According to this configuration, the illumination section has a long illumination lifetime and excellent maintenance characteristics.

The scattering plate 404 is provided in order to uniformize the light irradiated from the light source 405, and is provided on the emission side of the light source 405. When white LEDs are arranged in a line as in this embodiment, the light utilization efficiency can be increased when the scattering plate 404 is configured such that there is a considerable diffusion effect in the arrangement direction (the longitudinal direction of the line) and a low diffusion effect in the direction orthogonal to the arrangement direction.

The half mirror 406 has a light-splitting face 406a that reflects the light emitted from the light source 405 to the specimen 5 side while transmitting light emitted along the optical axis 400 from the specimen 5, thereby splitting the optical path into an illumination optical system and a light-receiving optical system. The half mirror 406 can include any optical element capable of splitting the optical path in this way and any suitable beam splitter can be used, e.g. a parallel flat-faced plate, a prism, etc.

A light-intercepting member, an aperture, or such like is provided as appropriate on the outer peripheral side of the half mirror 406 to restrict unwanted light.

In particular, a slit 403 is provided between the half mirror 406 and the scattering plate 404, and restricts unwanted light in the short direction with respect to the beam that spreads in a band-like shape after being diffused by the scattering plate 404. This can reduce the effects of bright field light on a dark field image.

The condensing lens 407 and the lens 409 are arranged in that order on the optical path of the band-like light that is turned back by the half mirror 406, and include lenses or lens groups having different powers in a face perpendicular to the paper and in a face parallel to the paper such as to form uniform illumination light in a band-like shape with a predetermined width at the inspection position, and also to condense the light emitted from the specimen 5 at the inspection position. Any suitable type of lens can be used; for example, a long cylindrical lens, a toric lens, an anamorphic lens, a lens including an adjustable face for reducing aberration, and such like, can be used in accordance with the length of the inspection position.

Various types of filters are provided between the condensing lens 407 and the lens 409 in order to restrict wavelength components that are not needed for observation, and a turret 408 is provided to switch the filters as appropriate within the optical path. The turret 408 includes a motor (not shown) for switching the arrangement of the filters, this switching being controlled by an optical system controller 507 explained below.

The illumination optical systems arranged in the optical holding section 202 (i.e., the light source 405, the scattering plate 404, the half mirror 406, the condensing lens 407, the lens 409, etc.) form an illumination section.

A light-receiving face of the light-receiving element 401 is arranged at an image-formation position of light that is emitted from the specimen 5, focused by the lens 409 and the condensing lens 407, and transmitted through the light-splitting face 406a of the half mirror 406; the light-receiving element 401 captures the image and converts it to an image-capture signal by photoelectric conversion, and therefore includes image-capturing elements such as CCDs arranged in a line.

A polarizing filter 402 is removably arranged on the optical path between the half mirror 406 and the light-receiving element 401 in order to enable polarized light observation.

These light-receiving optical systems (i.e., the lens 409, the condensing lens 407, the half mirror 406, the polarizing filter 402, the light-receiving element 401, etc.) form a light-receiving section.

Since the illumination/light-receiving optical system 410 thus forms an illumination optical system and a light-receiving optical system that share the main optical elements, namely the condensing lens 407 and the lens 409, the longitudinal-directional sizes of the light source 405 and the light-receiving element 401 can be aligned by arranging them at optically conjugate positions. This has advantages over arranging them at non-conjugate positions, in that the size of the optical holding section 202 can be reduced and the device can be made compact.

However, if unevenness in the light source 405 is comparatively large, it can be deviated slightly from the optically conjugate position. Since this defocuses the illumination light at the inspection position, illumination unevenness can be reduced and the illumination can be uniformized.

Effects of the illumination light-receiving section 21 of this embodiment will be explained.

As shown in FIG. 2A, when a regular pattern 30 having a pitch P exists on the flat specimen 5, if a beam 31a with a wavelength λ is irradiated onto the surface of the specimen 5 at an incident angle having a complement α, it is emitted at an exit angle having a complement β as diffracted light 31b.

Since a condition for generating such diffraction is that the path difference is an integral multiple of the wavelength λ, this establishes an equation:

$$P \cdot (\cos \beta - \cos \alpha) = n\lambda \quad (1)$$

where n is an integer (and similarly below).

Equation (1) is transformed to obtain Equation (2).

$$\cos \beta = (n\lambda/P) + \cos \alpha \quad (2)$$

Equation (2) indicates that the diffracted light 31b has a discrete angle β that is determined according to the wavelength λ and the pitch P of the pattern 30. Generally, with respect to n=0, 1, 2, . . . , the light is termed n-order diffracted light in each case. Zero-order diffracted light is specular reflected light.

The n-order diffracted light when n has a value other than zero reacts sensitively to fluctuations in the pitch of the pattern 30 and changes in the reflectivity of the specimen 5, whereby the intensity of the diffracted light varies. Therefore, an image is observed in the diffraction direction and compared with a normal image, the top of the pattern 30 becomes easier to detect and defect inspection is easier. Accordingly, diffracted light is conventionally use in defect inspection.

However, when the specimen 5 is not flat, interference is likely to occur between diffracted lights from the pattern 30, causing noise on the image and making it impossible to detect defects precisely.

This invention focuses on Bragg's law, with the optical axes of an illumination optical system (illumination section) and a light-receiving optical system (light-receiving section) in the illumination light-receiving section 21 being arranged partially coaxially, such that the specimen 5 exerts no influence even if it is not flat. This effect is explained below.

FIG. 2B simplifies the explanation by illustrating the relationship between incident light 32a and diffracted light 32b when a regular pattern 30 is formed on a permeable curved face 51 including minute undulations around a virtual flat face 50.

Here, pattern 30A is the pattern on the virtual flat face 50, γ is the incident angle of the incident light 32a, and δ is the exit angle of the diffracted light 32b. A pattern 30B is adjacent at pitch P and is formed on the curved face whose gradient angle can be approximated to ø.

At this time, when the path difference is determined from the geometric relationship and conditions for diffracted light are imposed, the following equation must be established.

$$P \cdot \{\sin(\gamma + \emptyset) + \sin(\delta - \emptyset)\}/\cos \emptyset = n\lambda \quad (3)$$

In Equation (3), γ is a function of δ, n, λ, and ø, and even if n, λ, and δ are constant, γ remains dependent on the gradient angle ø which differs according to location. Therefore, the undulation (degree of flatness) of the curved face changes the intensity of the diffracted light, and becomes noise during defect inspection.

When Equation (3) is transformed by an addition theorem for a trigonometric function, Equation (4) is obtained.

$$P \cdot \{(\sin \gamma + \sin \delta) + (\tan \emptyset) \cdot (\cos \gamma - \cos \delta)\} = n\lambda \quad (4)$$

In Equation (4), if ø=0, this indicates that the curved face 51 is flat and corresponds to FIG. 2A, and therefore the following equation similar to Equation (1) is obtained. The apparent difference to Equation (1) is due to the definition of the angle.

$$P \cdot (\sin \gamma + \sin \delta) = n\lambda \quad (5)$$

The following equation must be satisfied as a condition for ensuring that the relationship of Equation (4) does not depend on the gradient angle ø.

$$(\cos \gamma - \cos \delta) = 0 \quad (6)$$

That is, $$\delta = \gamma \quad (7)$$

must be established. Equation (4) now becomes Equation (8).

$$2 \cdot P \cdot \sin \gamma = n\lambda \quad (8)$$

This condition is known as Bragg's Law.

While the above describes a permeable curved face 51, the same goes for a reflecting face, without loss of generality.

Therefore, diffracted light that is diffracted in the same direction as the incidence direction is not affected by the degree of flatness of the surface, and, as shown by Equation (8), is emitted in a direction determined only by the pitch P of the pattern, the diffraction order n, and the wavelength λ.

In this image-capturing step of this embodiment, since it is possible to irradiate at various incident angles γ by rotating the optical holding section 202, and to measure the diffracted light established when the exit angle δ in the same direction as the incident angle becomes δ=γ, the image can be captured without being influenced by the degree of flatness.

Since the optical paths of the illumination optical system and the light-receiving optical system are shared and move together at this time, problems such as difficulty in measuring specific diffracted light due to interference between the light-receiving element 401 and the light source 405 can be solved. Therefore, an image of the diffracted light generated within the same range as the variable range of the incident angle can be captured throughout the entire rotatable range of the optical holding section 202.

Subsequently, a schematic configuration of the controller/processor 22 will be explained with reference to the functional block diagram of FIG. 3. Incidentally, the specific configuration of each functional block is realized by known unit such as electrical circuits, devices, microcomputers, and combinations thereof.

The schematic configuration of the controller/processor 22 includes a device controller 501 that controls the entire device, a manipulation section 511 that inputs control information from the outside to the device controller 501, other controllers controlled by the device controller 501, a display section 510, and a storage section 503 that stores an image-capture signal obtained by the light-receiving element 401 as two-dimensional image data. The targets (not shown) of control by the other controllers are provided inside and outside the controller/processor 22.

The other controllers include an illumination controller 504, a stage controller 505, a filter controller 506, an optical system controller 507, a sample direction alignment detector 508, an image-capture controller 502, a communication controller 522, and inspection algorithm sections 512A and 512B. A defect dictionary 519 and a defect determining section 518 are also provided.

The illumination controller 504 controls the light quantity in accordance with a control signal from the device controller 501 such as to match the light source 405 (see FIG. 1) to an image-capture timing with a light quantity that satisfies the capture conditions. This embodiment utilizes light quantity control that varies a flash duty ratio by controlling the ignition times of the LEDs.

The stage controller 505 controls operations of the stage 201 (see FIG. 1) in accordance with a control signal from the device controller 501, controlling the sticking and cancellation of sticking of the specimen 5 mounted on the stage 201, the on/off operation of the movement of the stage 201, and the speed of its movement. Operations of the stage 201 include, where necessary, rotating the specimen 5 in a direction that produces diffracted light, raising and lowering the specimen 5 using lift pins, etc.

The filter controller 506 switch-controls the filters of the illumination/light-receiving optical system 410 in accordance with a control signal from the device controller 501. That is, it switches the filters on the turret 408 by rotating the turret 408, and directs the polarizing filter 402 to and from the optical path.

The optical system controller 507 activates the holding section moving mechanism 202a and varies the angle of the optical holding section 202 in accordance with a control signal from the device controller 501.

The sample direction alignment detector 508 detects the set direction of the specimen 5 and whether there is any deviation from the set position, in accordance with a control signal from the device controller 501. For example, a position detecting sensor detects positions of flat orienters, notches, and the like that are provided for positioning the specimen 5, and outputs a detection signal indicating whether there is deviation from the predetermined position and the amount of deviation to the device controller 501.

In accordance with a control signal from the device controller 501, the image-capture controller 502 outputs an image-capture control signal to the light-receiving element 401, controls the image-capturing operation and image-capture conditions such as image-capture timings and exposure times, controls reading of the image-capture signal, and transmits an image-capture signal read from the light-receiving element 401 to the storage section 503.

Controls of image-capture timing and reading an image-capture signal will be explained with reference to FIG. 4.

Figure 4:
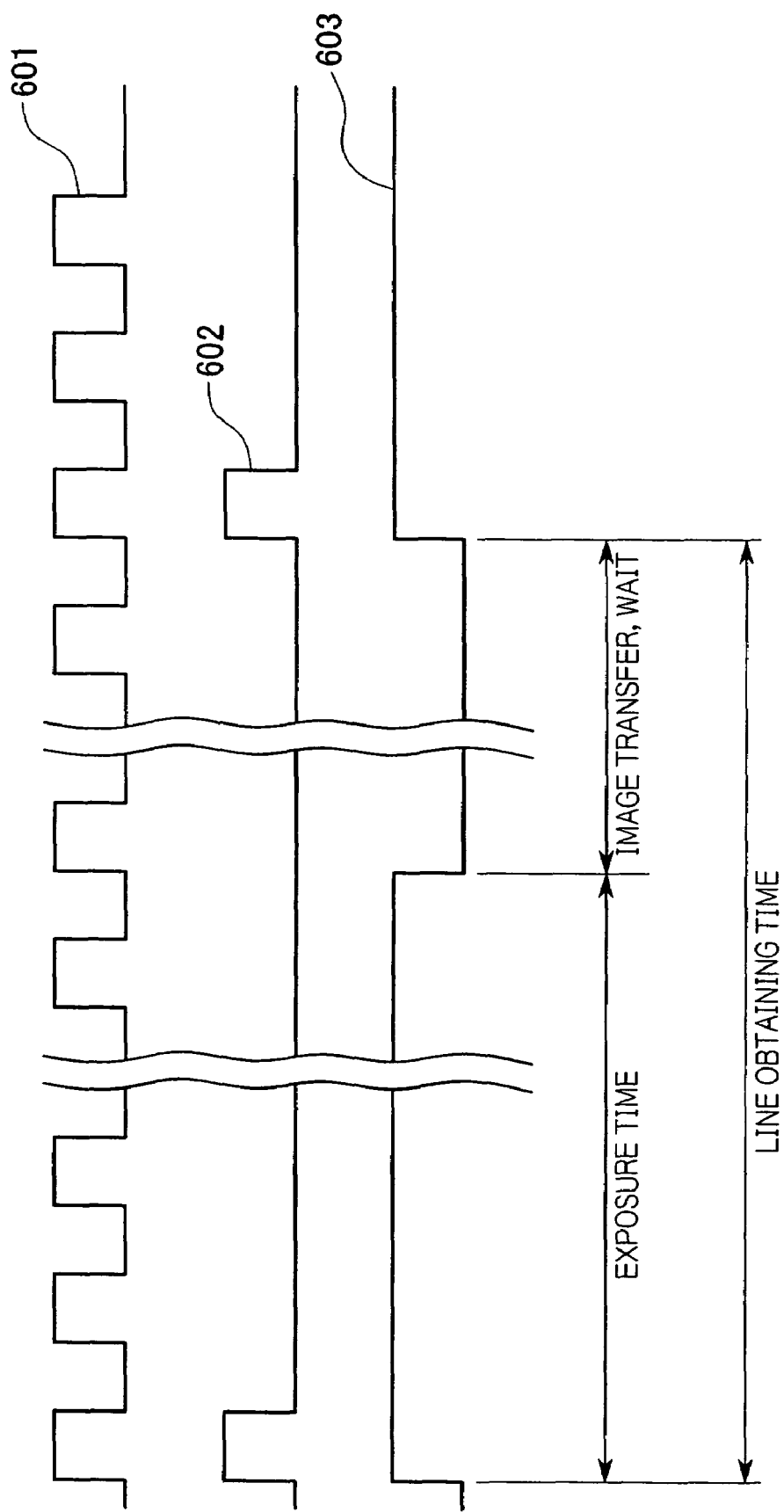
FIG. 4 is a schematic diagram of a timing chart for explanation of capture timing and read control of a capture signal of the defect inspection device according to the first embodiment of the invention.

FIG. 4 is a timing chart for explanation of controls of image-capture timing and reading an image-capture signal.

A clock signal 601 is a reference for operations of the light-receiving element 401.

A trigger signal 602 is a pulse-like control signal that is output from the image-capture controller 502 to the light-receiving element 401 at a given timing in synchronism with the clock signal 601. The light-receiving element 401 switches between start and end of image-capturing when the trigger signal 602 is high.

An exposure signal 603 is a variable-length control signal output from the image-capture controller 502 to the light-receiving element 401, in synchronism with the clock signal 601, in order to control the exposure time. The exposure signal 603 becomes high in synchronism with the trigger signal 602 that indicates the image-capture start, and remains high during the exposure time. The light-receiving element 401 performs an exposure operation only while the exposure signal 603 is high.

The exposure time is controlled by the image-capture controller 502 in accordance with the quantity of light emitted from the specimen 5 and the image-capture sensitivity of the light-receiving element 401 such that an image of the specimen 5 is properly captured.

The image-capture time determined by the intervals in the trigger signal 602 becomes the line obtaining time of the light-receiving element 401, and (line obtaining time—exposure time) becomes the image transfer time. That is, during this time, the stored charges of the image-capturing element are read sequentially, A/D converted, and transmitted to the image-capture controller 502.

The communication controller 522 controls communications to the device outside in accordance with a control signal from the device controller 501. For example, when the defect inspection device 20 is incorporated in a manufacturing device of the specimen 5, the communication controller 522 performs communication of control signals and data, and realizes coordinated operations based on communication procedures of the manufacturing device. Also, for example, when the device outside is a communication line such as a LAN, the communication controller 522 ensures that communication of control signals and data on can be performed on the communication line in compliance with a communication procedure of the communication line.

In accordance with respective control signals from the device controller 501, the inspection algorithm sections 512A and 512B perform image processing by reading image data stored in the storage section 503, extract defects, and output characteristic data of the defects to the device controller 501. The algorithms for defect extraction that they realize are identical, and can operate in parallel.

The inspection algorithm section 512A is explained below, while the inspection algorithm section 512B is not explained.

The inspection algorithm section 512A includes an image unevenness correction section 513, a distortion correction section 514, an image position correction section 515, a defect extractor 516, and a defect characteristic extractor 517, image data from the storage section 503 being transmitted between them in that order such that image processes for extracting defects are performed sequentially.

The image unevenness correction section 513 performs shading correction to correct differences of each pixel caused by characteristics of the light-receiving element 401 and the illumination/light-receiving optical system 410, based on parameters stored in a preset correction data storage section 521.

Accordingly, image information arising from illumination unevenness of the light source 405, variations in characteristics of the light-receiving element 401 and so on, is obtained beforehand by taking a correction reference sample and performing image processing, and is stored in the preset correction data storage section 521.

The distortion correction section 514 corrects image distortion caused by distortion of the illumination/light-receiving optical system 410 based on correction data stored in a characteristics storage section 520, and luminance correction for absorbing changes in the luminance due to variations in the specimen 5 and changes in the illumination/light-receiving optical system 410.

The image position correction section 515 performs image correction such as a position correction process of the specimen 5.

Image data processed by these sections can be stored in the storage section 503 when each process ends.

The defect extractor 516 can extract defects of the specimen 5 by comparing an image of the specimen 5 stored in the storage section 503 with a non-defective image stored beforehand in the storage section 503.

In addition to a comparative inspection of a non-defective image, the defect extractor 516 can execute an extraction method of detecting defects by fragmenting the image of the specimen 5, constructing a non-defective image by deeming a greatly contained portion to be non-defective, and comparing this constructed image with the image of the specimen 5.

The defect characteristic extractor 517 analyzes shape information and positional information of defects extracted by the defect extractor 516, and extracts characteristics of the defects.

The defect dictionary 519 is a searchable data storage section that stores categories of currently known defect information for identifying types of defects.

The defect determining section 518 determines defect categories by referring to data in the defect dictionary 519 in regard to shape information and positional information of defects whose characteristics are extracted using the inspection algorithm sections 512A and 512B. Defect types are preferably categorized based on characteristics arising in separate manufacturing steps of the specimen 5. This is advantageous in that it enables the defects to be correlated with the manufacturing steps, and helps identify their causes.

The display section 510 displays control information input from the manipulation section 511, images obtained by the light-receiving element 401, images of defects extracted using the inspection algorithm sections 512A and 512B, illumination result information, and the like, on a screen. That is, it forms a user interface of the defect inspection device 20.

Subsequently, an operation of the defect inspection device 20 will be explained. As explained above, since operations and the like of the controllers are controlled by the device controller 501, the transmission of respective control signals from the device controller 501 will be not be explained unless there is a danger of confusion.

Basic operations of the defect inspection device 20 include a specimen loading step, an initialization step, an image-capturing step, and a defect inspection step, these steps being performed in that order.

In the specimen loading step, a substrate before or after implementing the manufacturing step is delivered as the specimen 5 onto the stage 201 by a robot for delivery or the like. It is then guided by an appropriate guide, attached by the attaching mechanism, and secured in position.

In the initialization step, the sample direction alignment detector 508 is operated to determine whether the specimen 5 is positioned accurately at the predetermined position. If there is positional deviation, the stage controller 505 operates the stage 201 and corrects the arrangement of the specimen 5.

The stage controller 505 then drives the stage 201 and moves the specimen 5 to the inspection position.

Meanwhile, based on inspection conditions that are input and set prior to starting inspection, illumination conditions of the light source 405, the angle position of the optical holding section 202, and the like, are initialized by operating the light-receiving element 401.

That is, the image-capture controller 502 activates the light-receiving element 401 and enables an image to be captured.

The filter controller 506 sets a predetermined combination of filters of the illumination/light-receiving optical system 410, and the illumination controller 504 adjusts the light quantity of the light source 405.

The optical system controller 507 drives the holding section moving mechanism 202a and based on the inspection condition relating to the normal line of the specimen 5, moves the optical holding section 202 to, for example, a position inclined at a predetermined angle $\theta_0$.

In this embodiment, the quantity of light is adjusted by setting the flash duty ratio of the LEDs included in the light source 405. This enables the quantity of light to be switched efficiently and speedily without suffering loss of light quantity, waiting for the light quantity to stabilize, etc.

Since the light quantity decreases when the continuous ignition time of the LEDs is too long, a stable light quantity can be obtained by making them flash as appropriate in this manner.

Since the image-capture controller 502 can control the exposure by changing the length of the exposure signal 603, it is possible to perform a computation of the image-capture signal of the light-receiving element 401 while changing the exposure signal 603, and adjust the time width of the exposure signal 603 such that the image-capture signal has an appropriate gain, instead of using the illumination controller 504 to adjust the light quantity.

To obtain an appropriate image of the specimen 5, selection regarding whether to control the light quantity or control the exposure time can be made freely.

For example, since the inspection takt can be made constant by varying the light quantity of the light source 405 according to the reflectivity of the specimen 5 and the like while keeping the exposure time constant, this type of mode is usually selected.

On the other hand, the inspection takt when reducing the light quantity can be shortened by keeping the light quantity of the light source 405 constant and varying the exposure time.

Therefore, using input from the manipulation section 511, it is preferable to set a high-speed mode that increases the light quantity of the light source 405 and shortens the exposure time, thereby maintaining an appropriate light quantity while accelerating the inspection takt.

Since the output of the light-receiving element 401 can be expressed as the product of illuminance and time, in order to obtain identical output with respect to specimens 5 of identical conditions, the flash duty ratio of the LEDs is inversely proportional to the exposure time. Therefore, the flash duty ratio and the exposure time are determined by storing optical characteristic parameters that are determined by inspection conditions such as the category, reflectivity, incident angle of the illumination light, and transmission characteristics of the filters, in the storage section 503, and correcting the time in accordance with these optical characteristic parameters.

This is advantageous in that the light quantity can be speedily adjusted, enabling the inspection time to be shortened.

Since the light quantity on the exposure time can be controlled simply by controlling the time when they are inversely proportional, control becomes easier due to fewer control parameters. As a result, control is easy.

After the initialization step ends, the image-capturing step is performed. That is, the stage controller 505 moves the stage 201 at a constant speed while the light-receiving element 401 captures an image.

The constant speed of the stage 201 is the speed which the exposure width of the inspection position moves at in synchronism with the cycle of the trigger signal 602, an image-capture signal corresponding to the exposure width of the inspection position being read by the image-capture controller 502 and sequentially transmitted to the storage section 503. The surface of the specimen 5 is thereby scanned, and a two-dimensional image of the specimen 5 is stored in the storage section 503.

At this time, as shown in FIG. 1, illumination light is irradiated along the optical axis 400 from the optical holding section 202 inclined at the angle $\theta_0$, and illuminates the specimen 5 at an incident angle of $\theta_0$.

Although some of the illumination light that reaches the surface of the specimen 5 is absorbed by the specimen 5, the remainder becomes reflected light or diffracted light at the incident angle $\theta_0$ generated by a minute regular pattern such as a circuit pattern formed on the specimen 5, and is output outside the specimen 5. Of these reflected and diffracted lights, light that is heading towards the optical axis 400 is incident to the illumination/light-receiving optical system 410, focused by the lens 409 and the condensing lens 407, transmitted through the switched filter and the polarizing filter 402, and received by the light-receiving element 401.

Therefore in this embodiment, even if the angle $\theta_0$ changes, reflected light and diffracted light traveling along the same axial direction as the incident direction are always received. Viewed macroscopically, while this reflected light is specular when $\theta_0=0$, it becomes part of the scattered light at other angles.

When the image-capturing step under these initialization conditions ends, the optical system controller 507 changes the gradient angle of the optical holding section 202 to, for example, an angle $\theta_1$, and repeats the image-capturing step. That is, it returns to the initial inspection position by resetting the stage 201, sets the optical holding section 202 to the angle $\theta_1$, adjusts the light quantity and the exposure time where necessary in the same manner as in the initialization step, and performs the image-capturing step in the same manner as above.

Thus an image is captured for each of the gradient angles $\theta_0, \theta_1, \ldots, \theta_{i-1}$, (i being an integral number) that are required during inspection.

When the turret 408 inserts a filter that enforces wavelength restrictions into the optical path, an image can be captured only under appropriate diffraction conditions. By switching the polarizing filter 402, the image can be captured by receiving only appropriate polarized light.

By obtaining a plurality of images for the same gradient angle $\theta_j$ (j being an integral number) by changing the conditions of the filters and the like where necessary, the defect detection precision can be increased.

A defect inspection step is performed when all the above image-capturing steps end, or in parallel with them.

In performing the defect inspection step, the image data of the specimen 5 stored in the storage section 503 during the image-capturing steps is sent to the inspection algorithm sections 512A and 512B in accordance with a control signal of the device controller 501, and is image-processed. Since the inspection algorithm sections 512A and 512B can perform parallel processing, different image data can be sent to them at appropriate timings and defects can be extracted from the respective image data. An image process performed by the inspection algorithm section 512A is explained below.

The image unevenness correction section 513 performs shading correction of the image data sent to the inspection algorithm section 512A, based on the parameters stored in the preset correction data storage section 521.

To enable other image data to be corrected continuously thereafter, the corrected image data is sent to the storage section 503 and stored in it. The stored image data is displayed on the display section 510 when necessary in accordance with a command from the manipulation section 511 (hereinafter, the same goes for all data stored in the storage section 503).

The distortion correction section 514 corrects distortion and luminance, and the image position correction section 515 performs a process of correcting positional deviation of the specimen 5. After each of these corrections, the image data is stored in the storage section 503.

The defect extractor 516 performs a comparison process such as obtaining the difference between the image data corrected by the image unevenness correction section 513, the distortion correction section 514, and the image position correction section 515, and the image data relating to a non-defective specimen 5 stored beforehand in the storage section 503, and extracts only defected images.

The defect characteristic extractor 517 extracts characteristics of defective images extracted by the defect extractor 516, and extracts shape information, positional information, and the like relating to defects. The extracted defect data is sent to the defect determining section 518.

Since this defect data contains specific defect characteristics that are extracted as information independent from information such as the position and arrangement on the specimen 5, it can be compared with defect data stored in the defect dictionary 519.

The defect determining section 518 compares the defect data sent from the inspection algorithm section 512A (512B) with the data in the defect dictionary 519, and determines the defect type. Based on a predetermined determination reference, it determines whether the result is pass or fail, and notifies the device controller 501. Information such as the pass/fail result, the defect type, positional information, and number are stored in the storage section 503 together with the manufacturing step and inspection conditions.

The defect inspection step thereby ends.

When the device controller 501 detects that one series of defect inspection steps ends, based on a notification from the defect determining section 518, it displays the inspection result together with necessary information and images on the display section 510.

When a pass is determined, the stage controller 505 cancels the attachment of the specimen 5 and delivers it outside the device. The above steps are then performed for the next specimen.

When a failure is determined, the next inspection is suspended, a necessary warning or the like is displayed, and the procedure enters a standby state for a command from the operator.

Thus according to the defect inspection device of this embodiment, an image can be captured of light emitted in all directions within the movable range of the optical holding section 202, and surface defects can be inspected precisely by obtaining an image using diffracted light that is not influenced by the degree of flatness of the surface of the specimen 5.

Subsequently, a manipulation method for performing the above operations will be simply explained.

Unless particular special-purpose manipulations and input devices are provided, the manipulation section 511 is manipulated by manipulating a virtual manipulation screen displayed on the display section 510. Input values for an all-purpose input device of the manipulation section 511, such as a keyboard, a mouse, and a joystick, form an interface reflected in real time on the virtual manipulation screen.

The virtual manipulation screen includes a graphics display section that displays inspection images and image processing data as required.

Before inspection, inspection conditions are input via the manipulation section 511. To identify the inspection conditions at this time, information such as the product type name and the step name is input.

For sake of convenience when setting similar inspection conditions, a diversion/editing mode is prepared such that previous inspection conditions can be diverted by retrieving them from the storage section 503, and only points to be changed are corrected. When inspection conditions are set in diversion/editing mode, a version number of the inspection conditions such as Ver. XX (XX being an appropriate number) is automatically appended to them, enabling previous created inspection conditions to be used without alteration.

To avoid work for the operator, the most recent input information remains on the manipulation screen to enable different items only to be changed. For items with version numbers, those with the most recent version numbers are displayed.

To set the inspection region of the specimen 5, the inspection region and mapping information of a pattern manufactured inside it are input. When a plurality of identical patterns are manufactured, the position can be adjusted by displaying the positional information overlaying a captured image.

An image is captured by pressing an image-capture start button provided on the manipulation section 511, thereby starting the image-capturing of the specimen 5, automatically modulating the light such as to obtain an appropriate light quantity, and displaying the modulation conditions on the display section 510 such that the manipulator can confirm them.

There are three inspection modes: specular reflected light, diffracted light, and dark field view; these are selected as required from the manipulation section 511. For example, a manipulation screen is displayed on the display section 510 and includes a check box for each inspection mode; a mode is selected by using a selection device of the manipulation section 511, e.g. a mouse.

In specular reflected light mode, in this embodiment, the optical holding section 202 is set such that the optical axis 400 faces in a direction perpendicular to the specimen 5.

In diffracted light mode, the gradient angle of the optical holding section 202 is changed in accordance with the order of the diffracted light used in the inspection, and the position of the stage 201 is adjusted such that the diffracted light can be optimally detected. For example, the stage 201 is rotated in a horizontal plane. This positional adjustment is determined automatically from the mapping information of the inspection position.

In dark field mode, an angle that does not detect specular reflected light and diffracted light is automatically detected and set as the angle of the optical holding section 202, in the same manner as the step of automatically detecting diffracted light.

When the illumination angle and the illumination position are adjusted in accordance with these inspection modes, the light quantity is adjusted automatically.

Preparation for starting image-capture thereby ends.

When preparation for starting image-capture ends, an inspection mode screen is displayed on the display section 510. The inspection mode screen displays the product type name, step name, version number, and the like that have been input, and enables inspection to be started by pressing an inspection start button.

When inspection ends, the captured image and the detected defect are displayed in overlay on the image.

Label numbers that identify the defects are displayed near the defective parts, and information such as the type of defect, its area, coordinates, category probability, and such like, are displayed on the screen in correspondence with each label number.

The screen includes input sections such as product type name, step name, and version number, it being possible to search inspection results stored in the storage section 503 at any time by inputting this information.

Second Embodiment

A defect inspection device according to a second embodiment of the invention will be explained.

Figure 5:
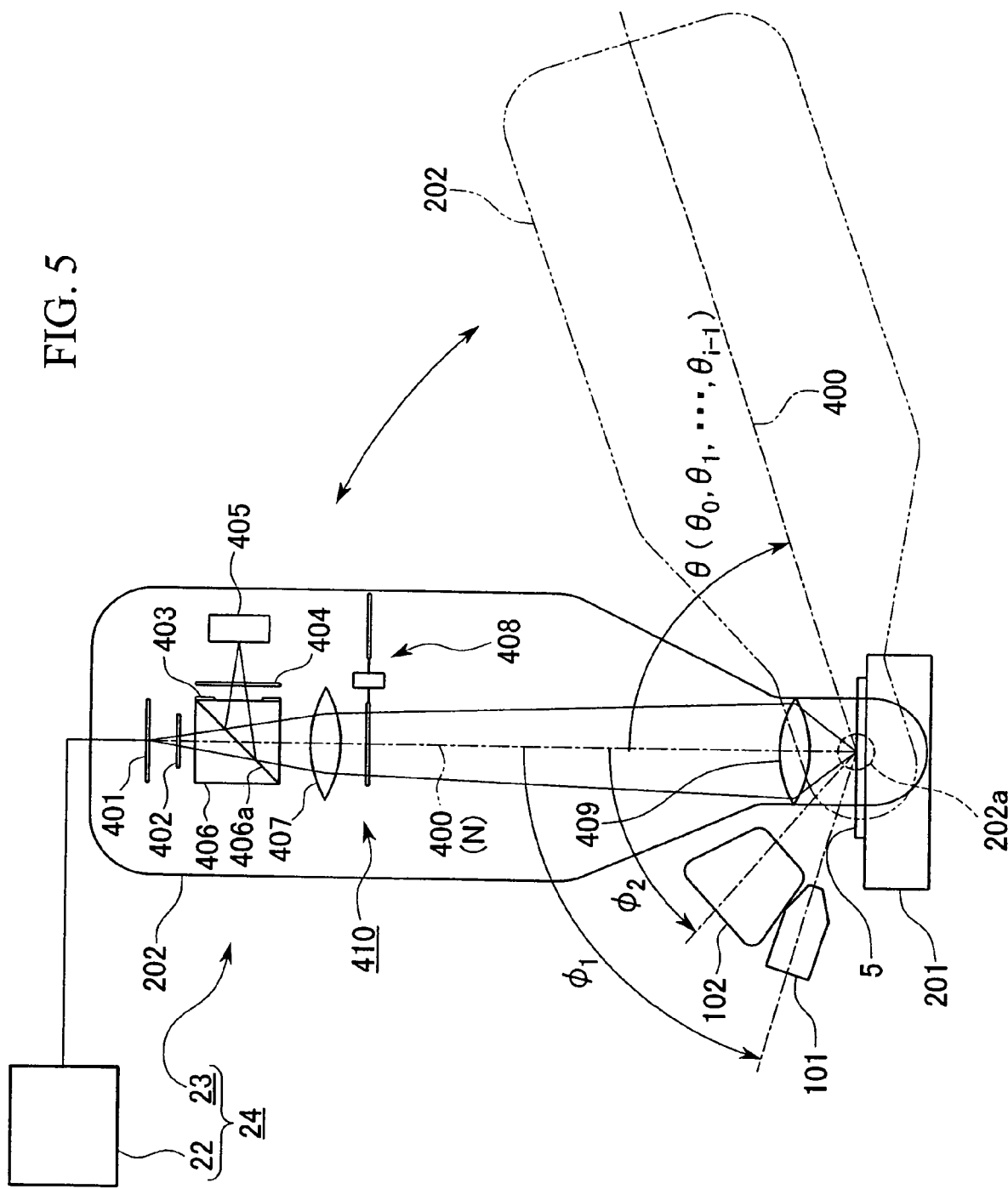
FIG. 5 is a conceptual diagram for explanation of a schematic configuration of a defect inspection device according to a second embodiment of the invention.
Figure 6:
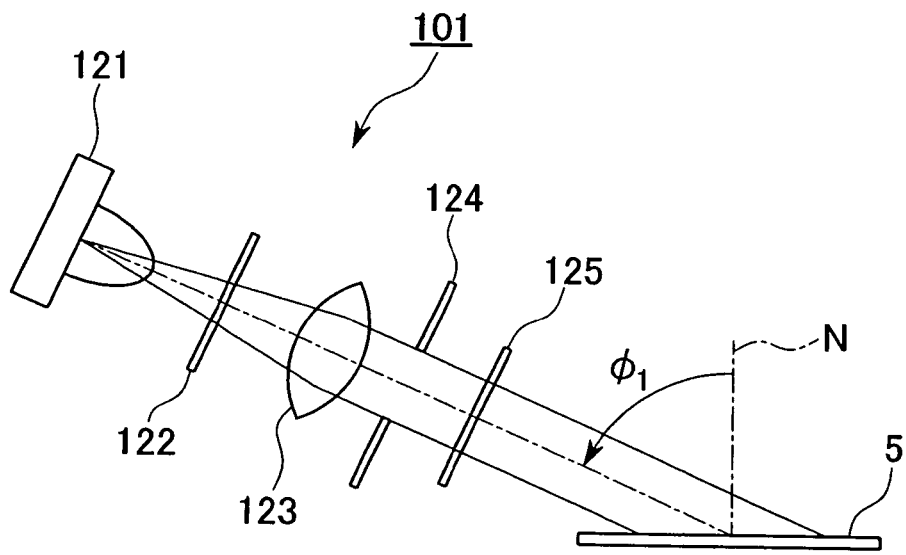
FIG. 6 is a basic explanatory diagram for explanation of one example of a plurality of illumination sections used in the defect inspection device according to the second embodiment of the invention.
Figure 7:
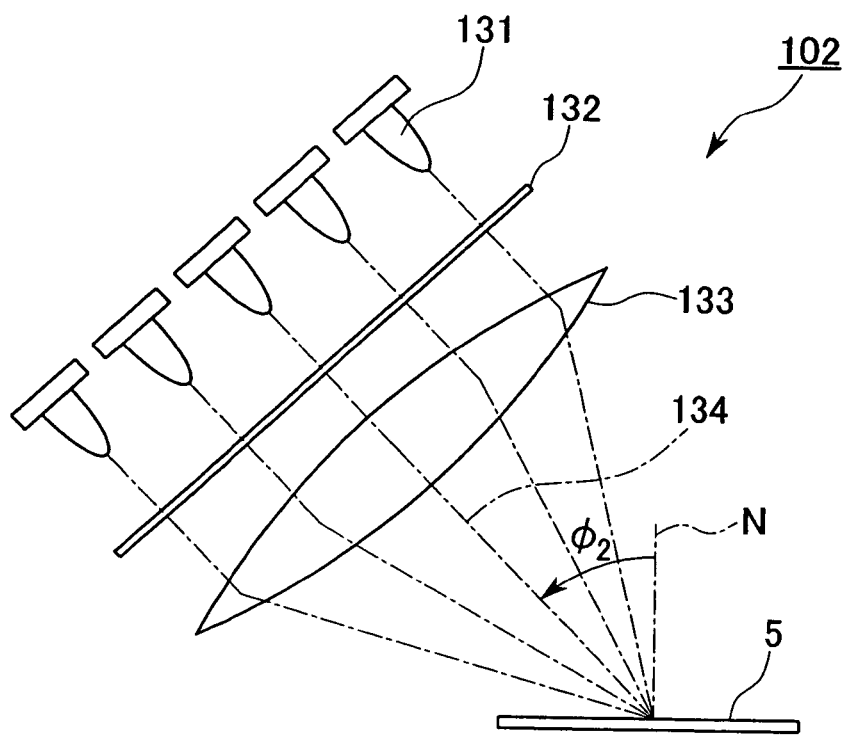
FIG. 7 is a basic explanatory diagram for explanation of another example of the same plurality of illumination sections.

FIG. 5 is a conceptual diagram for explanation of a schematic configuration of a defect inspection device according to the second embodiment of the invention. FIG. 6 is a basic explanatory diagram of one example of a plurality of illumination sections used in the defect inspection device according to the second embodiment of the invention. FIG. 7 is a basic explanatory diagram of another example of the same plurality of illumination sections.

As shown in FIG. 5, a defect inspection device 24 of this embodiment includes an illumination light-receiving section 23 instead of the illumination light-receiving section 21 of the illumination light-receiving section 21 of the first embodiment. The illumination light-receiving section 23 includes an illumination light-receiving section 21, and illumination sections 101 and 102 (at least one of a plurality of illumination sections).

In FIG. 5, a solid line represents the optical holding section 202 and the like when the optical axis 400 is at a position that overlaps with the normal line N of the specimen 5 in the same arrangement as FIG. 1.

The following explanation centers on points of difference with the first embodiment.

As shown in FIG. 5, the illumination section 101 is arranged at a position inclined at an angle $\varnothing_1$ with respect to the normal line N of the specimen 5, such that the illumination light can be emitted toward the inspection position. As shown in FIG. 6, the illumination section 101 includes an LED 121, a scattering plate 122, a lens 123, a slit 124, and a filter 125.

The LED 121 includes a plurality of white LEDs similar to the light source 405, which are arranged in the sheet depth direction of FIG. 6.

Since the scattering plate 122 scatters and uniformizes the light emitted from the LED 121, it is arranged extending along the sheet depth direction, and its scattering face is adjusted such that diffused light is obtained uniformly in depth direction that matches the arrangement of the LED 121 (longitudinal direction of inspection position).

The lens 123 is an optical element that condenses the lights diffused by the scattering plate 122 into approximately parallel lights.

The slit 124 intercepts unwanted light in the parallel lights emitted from the lens 123, and shapes the illumination light into a rectangular shape.

The filter 125 is a filter element that limits the wavelength of the beam transmitted through the slit 124 as necessary, and restricts the polarized component.

The illumination section 102 makes the illumination light incident on the inspection position from a wide range of angles, and thereby enables scattering illumination. As shown in FIGS. 5 and 7, the communication controller 102 is arranged such that illumination light can be emitted toward the specimen 5 while being centered on a position inclining at an angle of $\varnothing_2$ ($\varnothing_2 < \varnothing_1$) with respect to the normal line N of the specimen 5. As shown in FIG. 7, the illumination section 102 includes an LED 131, a scattering plate 132, and a lens 133. Reference numeral 134 represents the optical axis of the illumination section 102.

The LED 131 includes a plurality of white LEDs similar to the light source 405, which are arranged around the optical axis 134 in cross-sectional view in FIG. 7, and a further plurality which are arranged in the sheet depth direction of FIG. 7.

The scattering plate 132 scatters and uniformizes the light emitted from the LED 131 in the same manner as the scattering plate 122.

The lens 133 is an optical element that condenses the light diffused by the scattering plate 132 toward the inspection position.

By providing the illumination sections 101 and 102, the defect inspection device 24 of this embodiment can inspect defects in the following manner.

Since the illumination section 101 irradiates the inspection position with illumination light at angle $\varnothing_1$, inspection can be performed without using the light source 405. In particular, inspection can be performed using light that is specular reflected with respect to the incident angle $\varnothing_1$. It is acceptable if the illumination section 101 can vary the angle $\varnothing_1$.

If the angle $\varnothing_1$ of the illumination section 101 is comparatively large, and the optical axis 400 is perpendicular to the specimen 5 or slightly inclined from a perpendicular, observation can be performed using dark field illumination. That is, since the illumination light of the illumination section 101 is reflected at a narrow angle with respect to the surface of the specimen 5, only light that is scattered by scratches, foreign matter, and the like on the specimen 5 reaches the light-receiving element 401, enabling these scratches and foreign matter to be clearly observed in a dark field. Therefore, defect images of scratches, foreign matter, and the like can be obtained with hardly any influence of the pattern and the like.

When the specimen 5 has a multilayered structure, the angle $\varnothing_1$ can be increased such that the illumination light is completely reflected at the interface between an upper layer film and a lower layer film. This ensures that the illumination light is completely reflected from the lower layer film, and obtains an image in which diffracted light is not generated by a pattern below the lower layer film. This is advantageous in that image processing for defect extraction is easier, and defects only in the upper layer film can be efficiently extracted.

If the filter 125 is a polarizing filter and its polarization characteristics with the polarizing filter 402 are adjusted, it is possible to detect only specific polarized components, and to detect only components that are sensitive to changes in the surface layer.

According to the illumination section 102, the specimen 5 can be illuminated with illumination light from many directions; in particular, since the NA can be increased, scattered light can be efficiently generated for irregular defects such as foreign matter and scratches. Therefore, it is easy to detect even minute foreign matter and scratches that do not easily generate scattered light when using one-directional illumination light such as that from the illumination section 101.

While the above explanation describes dark field illumination using an illumination optical system including only the illumination sections 101 and 102, the detection precision of minute foreign matter and scratches can be further enhanced by applying the illumination light from the illumination sections 101 and 102 after setting the light source 405 to conditions for dark field illumination.

Figure 8:
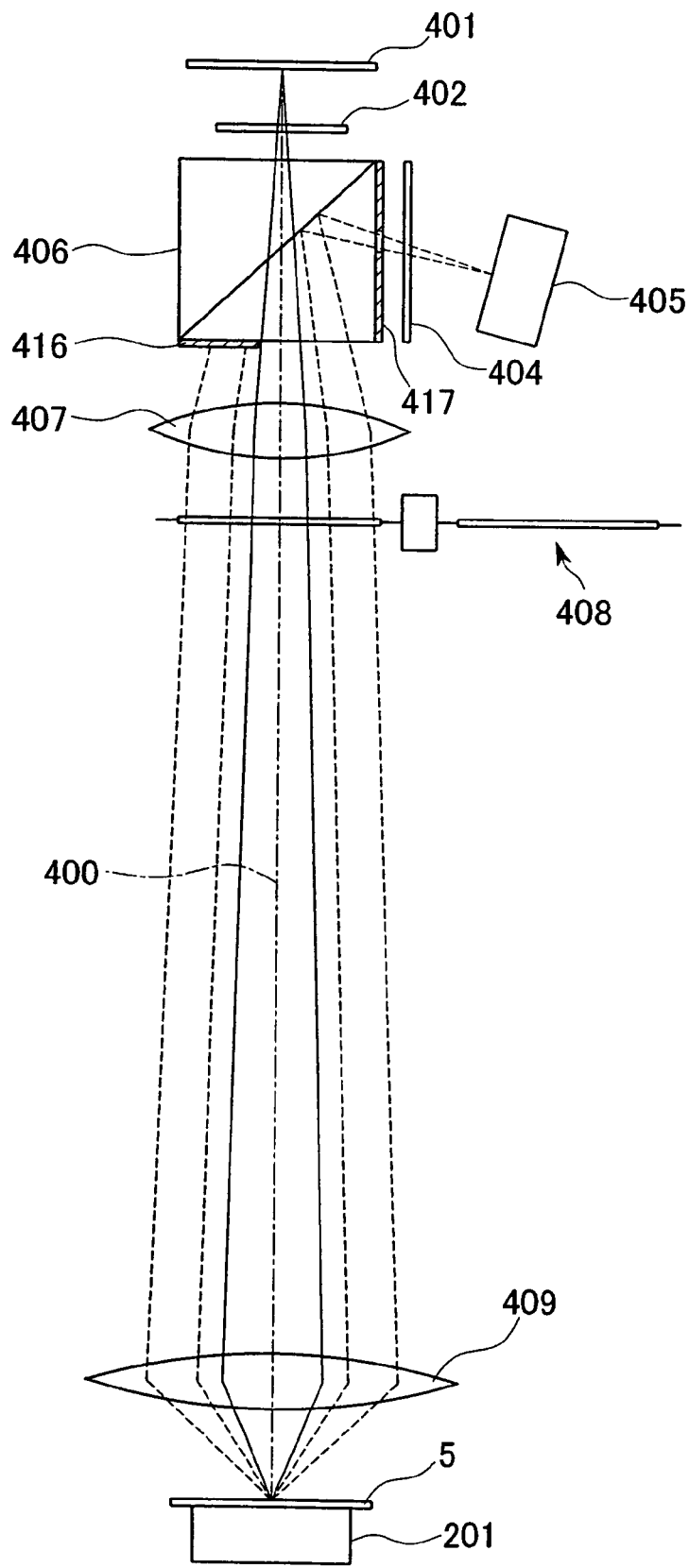
FIG. 8 is a configuration diagram of an optical system when performing dark field visual observation.

FIG. 8 is a configuration of an optical system when performing dark field observation. Although the configuration is basically the same as that of the illumination light-receiving sections 21 and 23, dark field observation is made possible by adding slits 416 and 417, since they prevent the specular reflected light from being incident on the light-receiving element 401.

That is, the slit 417 makes the illumination light follow an optical path that differs from the optical axis 400, and the illumination light is then inflected by the lens 409 such that it becomes incident on the specimen 5 at a comparatively incident angle that is suitable for dark field observation. Specular reflected light in the illumination light follows an optical path that differs from the optical axis 400, is made incident on the condensing lens 407, and is intercepted by the slit 416, whereby it is not incident on the light-receiving element 401.

Figure 9:
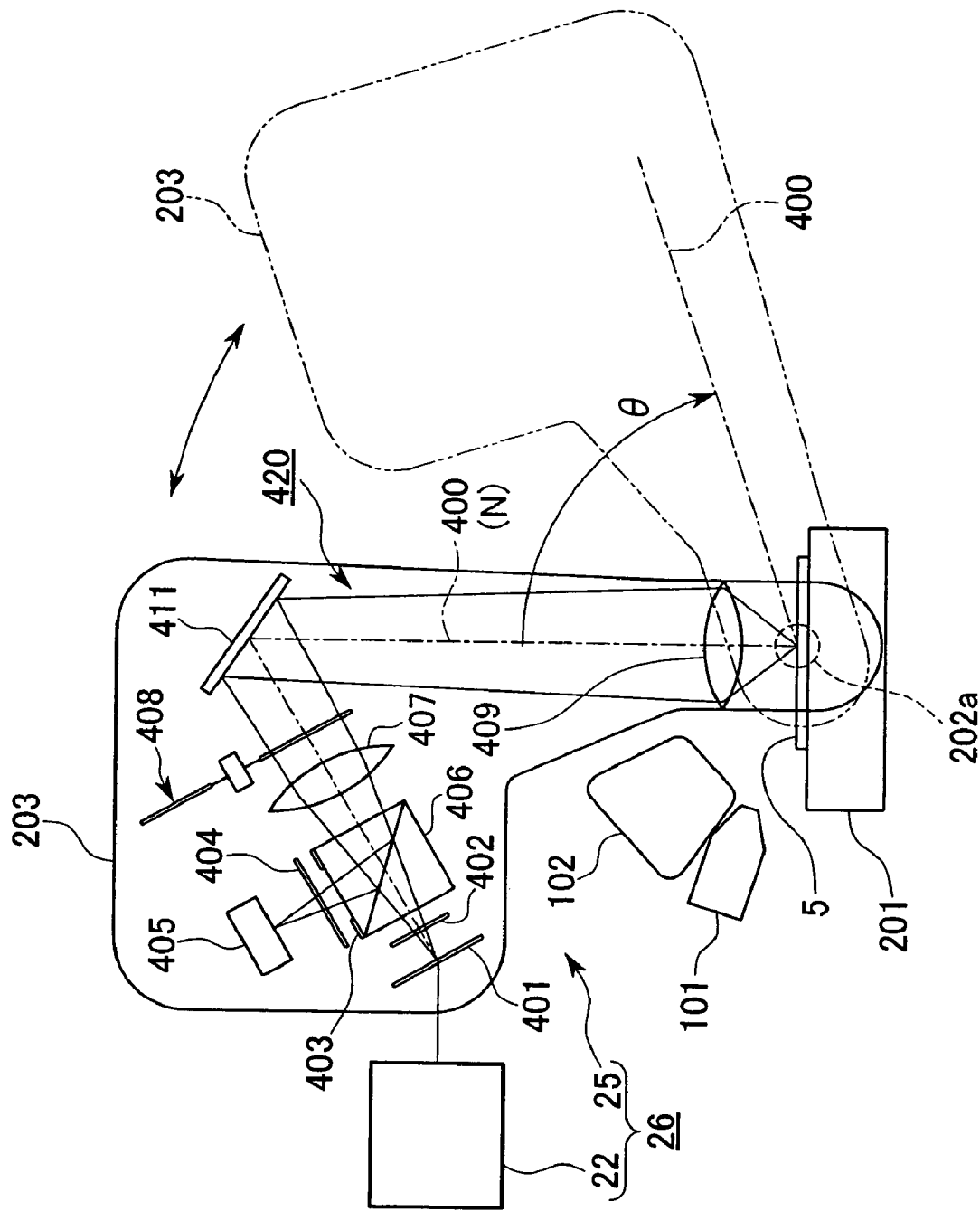
FIG. 9 is a conceptual diagram for explanation of a schematic configuration of a defect inspection device according to a modified example of the second embodiment.

Of the lights emitted from the light source 405 of the illumination light-receiving sections 21, 23, and 25 of FIGS. 1, 5, and 9, the slit 407 need only intercept at least the rays that are incident to the optical path, while the slit 416 need only intercept at least the rays that pass through the slit 417 and are specular reflected by the specimen 5. Also, the slits 416 and 417 can be provided with slide functions such that they can be attached and removed.

Subsequently, a modified example of this embodiment will be explained.

FIG. 9 is a conceptual diagram for explanation of a schematic configuration of a defect inspection device according to a modified example of the second embodiment.

As shown in FIG. 9, a defect inspection device 26 includes an illumination light-receiving section 25 instead of the illumination light-receiving section 23 of the defect inspection device 24 of the second embodiment.

The illumination light-receiving section 25 includes an optical holding section 203 instead of the optical holding section 202 of the illumination light-receiving section 21, and the optical holding section 203 includes an illumination/light-receiving optical system 420 that folds the optical path of the illumination/light-receiving optical system 410.

The illumination/light-receiving optical system 420 includes a mirror 411 (reflecting member) between the condensing lens 407 and the lens 409, whereby the optical path is folded into a V-shape and the light-receiving element 401 is arranged above the illumination section 102 and the illumination section 101 in alignment with the normal line N of the specimen 5.

The optical holding section 203 is a casing that accommodates the illumination/light-receiving optical system 420 folded in that manner, and is movably supported by the holding section moving mechanism 202a in the same manner as the optical holding section 202.

According to this configuration, the optical holding section 203 can be made compact and provided above the illumination sections 101 and 102, whereby the movable range of the optical holding section 203 can be made comparatively large.

While in FIG. 9, the optical path bends in a direction parallel to the sheet, it can be bent within a face perpendicular to the sheet. This can increase the range of the rotation angle.

Furthermore, while semiconductor wafers, liquid crystal substrates, and the like are recently tending to be made larger in order to reduce costs, since this configuration enables the defect inspection device to be made compact even when the illumination/light-receiving optical system 420 has a long optical path, the space required for inspection can be kept within a narrow range even if the size of the specimen 5 increases.

Third Embodiment

A defect inspection device according to a third embodiment of the invention will be explained.

Figure 10:
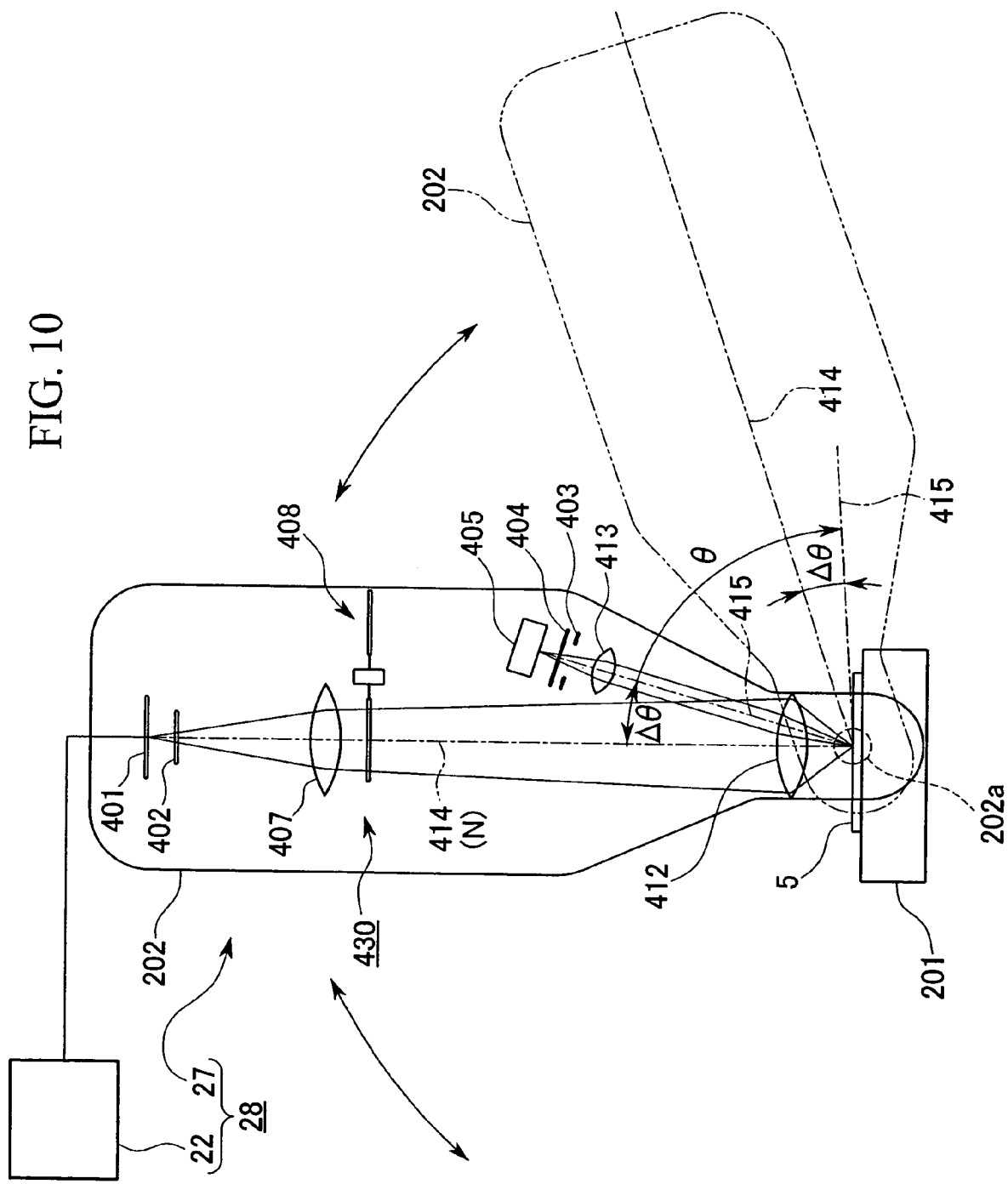
FIG. 10 is a conceptual diagram for explanation of a schematic configuration of a defect inspection device according to a third embodiment of the invention.

FIG. 10 is a conceptual diagram for explanation of a schematic configuration of a defect inspection device according to a third embodiment of the invention.

As shown in FIG. 10, the defect inspection device 28 of this embodiment includes an illumination light-receiving section 27 instead of the illumination light-receiving section 21 of the defect inspection device 20 of the first embodiment. The illumination light-receiving section 27 includes an illumination/light-receiving optical system 430 instead of the illumination/light-receiving optical system 410 of the first embodiment.

The following explanation centers on points of difference with the first embodiment.

The illumination/light-receiving optical system 430 includes a light-receiving optical system that excludes the half mirror 406 of the illumination/light-receiving optical system 410 of the first embodiment, and includes a lens 412 instead of the lens 409. This light-receiving optical system condenses light emitted from the specimen 5 along an optical expressed by an optical axis 414, and leads it onto the light-receiving element 401.

In addition to the light source 405, the scattering plate 404, and the lens 412, the illumination light-receiving optical system also includes a condensing lens 413 that approximately collimates the light diffused by the scattering plate 404 and makes it incident on the lens 412, thereby functioning as an optical system that can irradiate an inspection position on the specimen 5 with illumination light from a direction inclined at an angle $\Delta\theta$ with respect to the optical axis 414.

The illumination/light-receiving optical system 430 is secured to the optical holding section 202, and held such that it can rotate around the holding section moving mechanism 202a. Therefore, when rotating, the angle formed by the optical paths between the illumination optical system and the light-receiving optical system is maintained at angle $\Delta\theta$.

Preferably, $\Delta\theta$ is a minute angle, and is preferably in the same direction as the incident angle of the illumination light. For example, it should be equal to or less than 15°.

Thus this embodiment is designed such that the lens 412 can be use in common with the light-receiving optical system and the illumination optical system. By providing the condensing lens 413, the optical paths of the light-receiving optical system and the illumination optical system can be set to different lengths. Therefore, since the illumination optical system capable of reducing aberration more than the light-receiving optical system can be made compact as shown in FIG. 9, there is an advantage that the overall device can be made smaller.

Furthermore, since the light-receiving optical system and the illumination optical system are not coaxial, even when their optical characteristics are difficult to satisfy, it is possible to concentrate on the different amounts of aberration correction required by each, and, for example, set the lens 412 such as to give priority to aberration correction of the light-receiving optical system, while using the scattering plate 404, the slit 403, or unit such as a suitable shading correction filter to correct the influence of aberration remaining in the illumination optical system, such as illumination unevenness.

Depending on the size of the angle $\Delta\theta$, it is possible to separate the optical path of the light-receiving optical system from the optical path of the illumination optical system such that they pass through lens faces having different optical characteristics. In this case, the lens 412 can include an adjustable lens, or a combination of two lenses glued together.

According to this configuration, as shown in FIG. 10, with the optical axis 414 aligned with the normal line N of the light source 405, light irradiated from the light source 405 passes along the optical axis 415 and is incident on the specimen 5 at the angle $\Delta\theta$. Light emitted by the specimen 5 in the direction of the optical axis 414 is then transmitted through the lens 412, the turret 408, the condensing lens 407, and the polarizing filter 402 in that order, is focused on the light-receiving element 401, and its image is captured.

By rotating the optical holding section 202, an image is captured of the light emitted in a direction deviating by angle $\Delta\theta$ when the specimen 5 is illuminated after changing the incident angle of the illumination light.

Consequently, specular reflected light and diffracted light within the angle range obtained by subtracting $\Delta\theta$ from the rotational angle range of the optical holding section 202 can be received, and defects can be extracted from their images.

An image can be captured from specular reflected light when the optical axes 414 and 415 are rotated to positions at an angle ($\Delta\theta/2$) from the normal line N of the specimen 5.

According to the defect inspection device 28 of this embodiment, using illumination light incident on the specimen 5 at an incident angle within the rotatable range of the optical holding section 202, it is possible to capture an image of light emitted in a direction deviated by a fixed angle $\Delta\theta$ to that incident direction, enabling an image of light emitted from the specimen 5 to be captured over a wide range.

Also, since the illumination optical system and the light-receiving optical system are configured separately, each can be configured as an optical system in accordance with the required precision, whereby they can be made smaller and inexpensive.

Where appropriate, the illumination sections 101 and 102, and the slits 416 and 417 for dark field observation of the second embodiment can be added, and the optical path can be folded by providing the mirror 411 of the modified example of the second embodiment.

Fourth Embodiment

Subsequently, a substrate manufacturing system according to a fourth embodiment of the invention will be explained.

Figure 11:
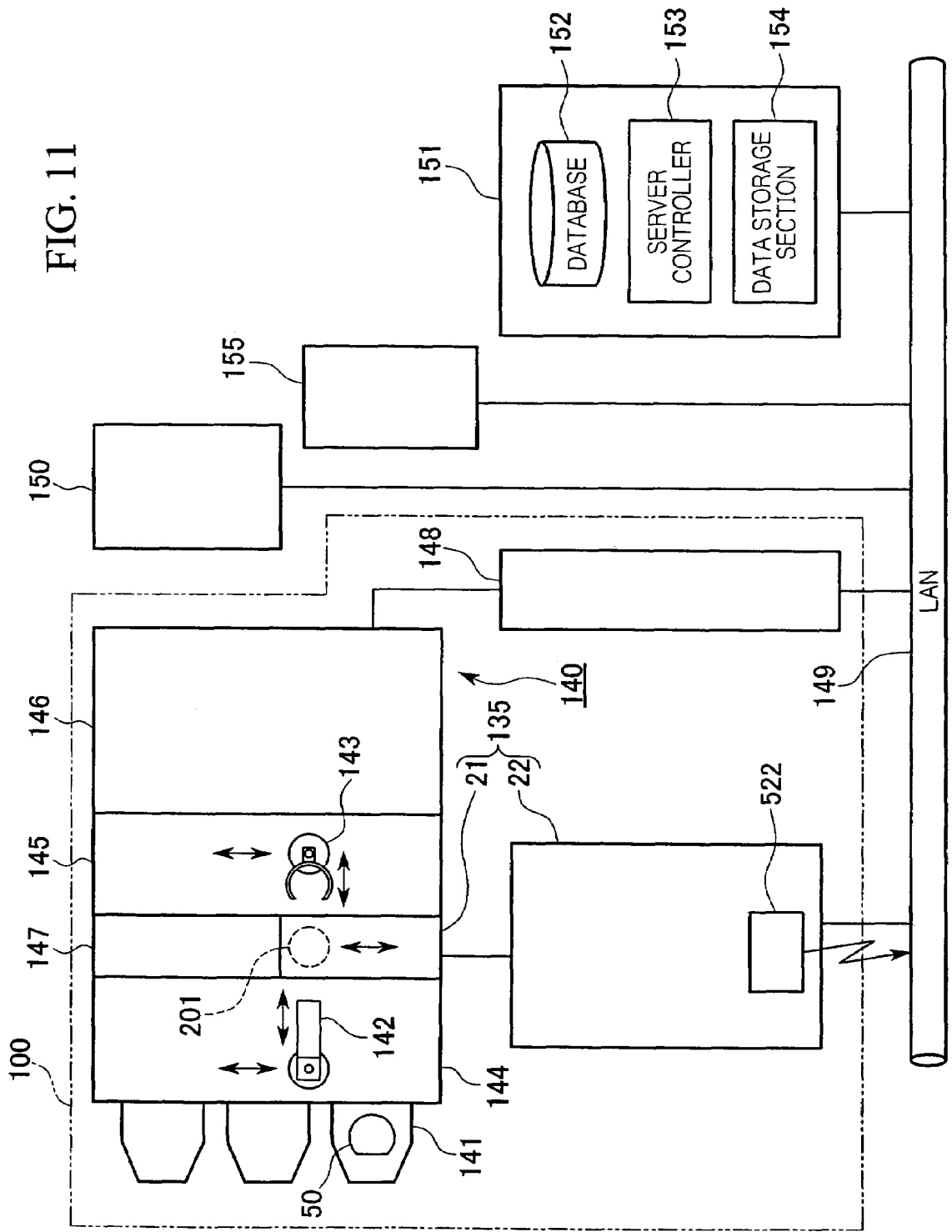
FIG. 11 is a conceptual diagram for explanation of a schematic configuration of a defect inspection device according to a fourth embodiment of the invention.

FIG. 11 is a conceptual diagram for explanation of a schematic configuration of a defect inspection device according to a fourth embodiment of the invention.

A substrate manufacturing system 100 of this embodiment incorporates the defect inspection device of the invention in a substrate manufacturing device that forms a circuit pattern on a semiconductor wafer substrate, and performs defect inspection using a substrate manufactured by the substrate manufacturing device as a specimen. The substrate manufacturing device is capable of automatic correction, and can make automatic corrections while incorporating inspection results of the defect inspection device.

The schematic configuration of the substrate manufacturing system 100 includes a substrate manufacturing device 140 and a defect inspection device 135 that is incorporated in the substrate manufacturing device 140.

The substrate manufacturing device 140 includes a delivery section 144 that inserts/removes a carrier 141 and a plurality of substrates 50 (specimens) that are delivered from the outside to and from a manufacturing step, a coating development section 146 that performs a coating development step to the substrates 50, an exposure section 147 that performs an exposure step to the substrates 50, a delivery section 145 that passes the substrates 50 to/from the defect inspection device 135, and a controller 148 that controls operations of the above sections.

The delivery sections 144 and 145 respectively include delivery robots 142 and 143 for holding and delivering the substrates 50. The delivery robots 142 and 143 can move within a horizontal plane above their respective delivery sections 144 and 145, and holding sections of the substrates 50 can expand and contract horizontally, move up and down, and rotate around a vertical axis.

The controller 148 controls manufacturing processes of the substrate manufacturing device 140, and also controls control parameters of each manufacturing process. It is connected to a LAN 149 consisting of an appropriate network line such as the internet, and can transmit control signals and data communications via the LAN 149.

The automatic correction unit contained in the controller 148 is notified of information relating to defect generation, and, in accordance with that information, can refer to information relating to a correlation between changes in the control parameters of each process and defect generation, and re-correct the control parameters.

The correlation between changes in the control parameters and defect generation is determined by tests beforehand and stored in a location where it can be referred to by the controller 148.

One example of a correlation between changes in the control parameters and defect generation is the appearance of imperfect shapes that are dependent on the figuration along mapping zones, and are caused by focus blurring and exposure irregularities during the exposure step.

While in this embodiment, the correlation is stored in storage unit in the controller 148, it can be stored outside, e.g. in a data storage section 154.

The defect inspection device 135 can be any type of device according to the defect inspection device of the invention; the following explanation describes a configuration similar to the defect inspection device 20 of the first embodiment.

The illumination light-receiving section 21 of the defect inspection device 135 is provided adjacent to the exposure section 147, and incorporated at a position where the delivery robots 142 and 143 can attach/remove the substrates 50 to/from the stage 201. Therefore, the substrates 50 delivered to the substrate manufacturing system 100 can be delivered as appropriate onto the stage 201 and inspected at any stage during the manufacturing step.

The controller/processor 22 of the defect inspection device 135 is connected via the communication controller 522 to the LAN 149, and can perform external control in accordance with manipulation of the manipulation section 511 and an inspection server 151 connected to the LAN 149.

Therefore, input information such as inspection conditions can also be input via the LAN 149 from the inspection server 151.

The inspection server 151 includes a server controller 153 and a data storage section 154, and the data storage section 154 includes a database 152 for storing inspection conditions and inspection results and searching them at any time.

On the LAN 149, a defect inspection device 150 having the same configuration as the defect inspection device of the invention, and a review microscope 155 that reviews defects and includes a communication controller capable of accessing the inspection server 151, are arranged on the manufacturing line as devices suitable for use together with the substrate manufacturing system 100.

An operation of the substrate manufacturing system 100 will be explained.

The substrate 50 delivered from the carrier 141 to the substrate manufacturing system 100 is delivered by the delivery sections 145 and 144 to the coating development section 146 and the exposure section 147, where it is subject to a coating development step and an exposure step. Before starting manufacture, and at a stage during any step where defect inspection of the surface becomes necessary (e.g. when one pattern has been formed), the delivery robots 142 and 143 deliver the substrate 50 onto the stage 201. At that time, the delivery robot 143 delivers the substrate 50 onto the stage 201 from the right side of FIG. 10.

Via various steps such as those described in the first embodiment, the illumination light-receiving section 21 performs defect inspection of the substrate 50, and, when further continuing the manufacturing step, the substrate 50 is delivered to the coating development section 146, the exposure section 147, and so on, these processes being repeated until all the manufacturing steps of the substrate 50 are completed.

When the last defect inspection of the manufacturing step of the substrate 50 ends, the controller 148 is notified that image-capturing has ended via the communication controller 522 and the LAN 149. The delivery robots 142 and 143 are activated, and the substrate 50 is delivered onto the stage 201 from the left side of FIG. 10, transferred to the carrier 141, and carried outside the substrate manufacturing system 100 when the carrier 141 becomes full.

Thus in this embodiment, since the delivery robots 142 and 143 are provided on the left and right sides of the stage 201, delivery to and from the defect inspection device 135 can be performed efficiently.

When a defect is detected in the substrate 50 during this inspection step, notification that a defect has been discovered is sent via the communication controller 522 to the controller 148, and defect information stored in the storage section 503 of the defect inspection device 135 such as the defect type, number, and position is transmitted to the controller 148.

When the controller 148 determines, in accordance with the defect information, that the defect can be improved using the control parameters of the manufacturing step, it corrects the control parameters.

When it determines that there is a problem in the exposure step, the controller 148 re-corrects the amount of exposure light of the exposure section 147, the focus amount, the tilt amount of the holding stand of the substrate 50, and so on, and, if these control parameters deviate from their predetermined values, returns them to their predetermined values.

For example, let us suppose that an improper defect, dependent on the figuration of the mapping zones and caused by focus blurring and irregularity in the amount of exposure light during the exposure step, is discovered.

In this case, in the exposure section 147, the focus is altered while detecting the amount of exposure light using a exposure light detection sensor or the like, and the focus position when the amount of exposure light is greatest is detected. The stage 201 is moved from there to a predetermined focus position. By resetting the amount of exposure light while detecting the amount of exposure light during exposure at that focus position, the focus amount and the amount of exposure light are re-corrected to proper settings.

Similarly, when a problem is detected in the development step of the coating development section 146, control parameters for the capacity, temperature, and the like of the developing solution are detected using a capacity sensor, a temperature sensor, and the like provided in the coating development section 146, while re-correcting them.

When the controller 148 determines that the correlation between the defect and the control parameters is unidentifiable due to the defect being cause by sticking of unidentifiable foreign matter and the like, or when there is no disruption in the control parameters even after re-correction, it notifies the operator that it has discovered a defect which cannot be solved by automatic correction. Also, when it determines that the defect will be remedied by reworking the substrate 50, it notifies the operator that reworking is necessary.

Thus in the substrate manufacturing system 100, since the controller 148 can automatically correct problems in the control parameters of the manufacturing step based on information relating to defects detected by the defect inspection device 135 incorporated in the coating development section 146, defect information can be speedily utilized in the manufacturing step, achieving advantages of reducing the level of defectiveness, reducing the number of inspectors during the manufacturing step or enabling it to be performed unmanned.

Subsequently, operations relating to the defect inspection device 150, the inspection server 151, and the review microscope 155 will be explained.

While the defect inspection device 150 can perform the same inspection as the defect inspection device 135, in this embodiment, it sets the inspection conditions and performs maintenance thereof instead of the defect inspection device 135, mainly by connection to the LAN 149. That is, the inspection conditions are input from the defect inspection device 150, which stores them, corrects them as appropriate, and performs maintenance of them in accordance with the manufacturing step.

These inspection conditions are transmitted as required to the defect inspection device 135 via the LAN 149.

Although when inputting the inspection conditions to the defect inspection device 135, since the inspection is performed in conjunction with the manufacturing step of the substrate 50 executed by the substrate manufacturing device 140, the manufacturing step must be stopped, when the inspection conditions are input using the defect inspection device 150, they can be set and modified without stopping the manufacturing step. This has advantages of increasing the operating rate of the substrate manufacturing device 140, and enabling the substrate 50 to be manufactured inexpensively.

According to the inspection server 151, by storing the inspection conditions and inspection results held in the defect inspection devices 135 and 150 in the data storage section 154, a database can be constructed, and accessed via the LAN 149. This can increase the efficiency of manufacturing and inspecting the substrate.

Data is registered in the database 152 as follows.

When the defect inspection device 135 (150) ends inspection, in compliance with a command from the device controller 501 (see FIG. 3), the inspection image and inspection data are stored in the data storage section 154 via the communication controller 522. After all data have been sent, a trigger file that acts as an end trigger is stored in the data storage section 154.

The server controller 153 constantly monitors the creation of the trigger file, and, when it detects a trigger file, stores image data of the corresponding inspection in the data storage section 154 in compliance with a standard format; in addition, it registers the inspection data as a record in the database 152.

For example, information such as a product type name, a step name, inspection conditions, a lot ID for identifying the lot, a manufacturing device ID for identifying the manufacturing device, inspection date, the name of the operation manager, and the storage location of the image data, are registered in the record such that they can be searched using various methods after registration.

By registering these data in the database 152, images corresponding to conditions relating to the data can be searched and displayed.

Various search engines and display software that are included in general-purpose web functions available on the internet and the like can be used in searching from the server controller 153 and displaying. This has an advantage of facilitating links to other inspection devices, without developing a search engine or the like that is specific to the LAN 149.

Since the inspection server 151 can simultaneously manage data of the defect inspection devices 135 and 150, the device controller 501 of the defect inspection device 135 can download, via the LAN 149, inspection conditions that are uploaded from the defect inspection device 150 to the server controller 153, to the defect inspection device 135.

Therefore, the defect inspection device 135 can download the inspection conditions that are appropriately maintained by the defect inspection device 150 when they are needed, and can allocate inspection and setting of the inspection conditions, thereby increasing the efficiency of the inspection step.

When there are a plurality of devices such as the defect inspection device 150 that can upload and download inspection conditions, data uploaded to the inspection server 151 is corrected by exclusion control performed by the server controller 153. That is, the inspection conditions are permitted only when the defect inspection device that first uploaded them brings up and updates the version number and the update date, correction uploaded by other devices not being permitted. This ensures consistency of the inspection conditions, and prevents them from being modified by other operators and defect inspection devices after they are created. It also becomes possible to manage modification histories of the inspection conditions.

Since the review microscope 155 is connected to the LAN 149, when reviewing a defect in a substrate 50 that a defect has been discovered in, information such as the position and size of the defect can be extracted from the database 152, and, based on this information, the position of the substrate 50 can be speedily moved such that a defect for review can be observed at an appropriate magnification.

If the result of observation is that the data of the defect in the database 152 is inappropriate, the data can be corrected by accessing the database 152. The server controller 153 permits correction of the database 152 by the review microscope 155, and retains a history in which the defect data has been modified according to the review result.

Thus, based on the review result, it is possible to increase the precision of defect data stored in the database 152 by changing the category name, correcting the size of the defect, and so on. Using this well-maintained, highly precise data, the manufacturing step and the inspection step can be managed precisely.

The review microscope 155 can include any device that enables precise observation of defects, e.g. a scanning electron microscope (SEM), a pattern-detection device, a superimposition device, a line-width inspection device, or a combination of these.

The defect inspection device of the invention includes the illumination section that irradiates a specimen with illumination light having a variable incident angle, and the light-receiving section that receives light from the specimen irradiated with illumination light from the illumination section with a variable detection angle, the light-receiving section receiving the light emitted in substantially the same direction as the direction of incidence of the illumination light from the illumination section.

According to this invention, at least at the time of inspection, since the light-receiving section receives the light emitted from the specimen illuminated by the light from the illumination section in substantially the same direction as the direction of incidence, the light-receiving section can always be arranged at the same angular position with respect to the illumination section even if the incident angle of the illumination light changes. As a result, interference between the illumination section and light-receiving section can be avoided within the variable range of the incident angle. Therefore, light emitted from the specimen can be detected within the same range as the variable range of the incident angle.

To achieve this configuration, the illumination section and the light-receiving section can be provided together such that their optical paths form a constant angle, or they can be allowed to move independently of each other while being controlled such that the angle formed by their optical paths during inspection is constant.

The constant angle need only be constant during each inspection, and its value can be made adjustable.

Preferably in the defect inspection device of the invention, the optical axis of the illumination section and the optical axis of the light-receiving section are partially coaxial.

In this case, since the optical axis of the illumination section and the optical axis of the light-receiving section are partially coaxial, the device can be made compact. Therefore, the variable range incident angle of the illumination light can be enlarged.

When the light detected by the light-receiving section is light diffracted from the illumination light, the incident angle of the illumination light and this diffracted light become coaxial and satisfy Bragg's law, whereby low-noise diffracted light that is not dependent on changes in the thickness of the specimen is received. Therefore, image processing becomes easier and the inspection precision can be enhanced.

Preferably in the defect inspection device of the invention, optical path splitting unit is arranged on an optical path of light that is emitted from the illumination section, irradiated to the specimen, and received from the specimen at the light-receiving section, whereby the optical axes are made partially coaxial.

In this case, since the optical splitting unit partially splits the optical path, arrangement of members on the optical paths is made easier even though they are partial coaxial.

In the defect inspection device of the invention, it is preferable to enable the illumination section and the light-receiving section to be rotated together.

In this case, since the illumination section and the light-receiving section can be rotated together, the light emitted from the specimen can be more reliably and easily received in the same direction as the incident direction of the illumination light, whereby the inspection efficiency can be increased.

Preferably in the defect inspection device of the invention, a reflecting member is provided on the optical path of the light emitted from the illumination section, irradiated to the specimen, and received from the specimen at the light-receiving section, whereby the optical path is folded.

In this case, since the reflecting member folds the optical path, members can be arranged more easily along the optical path and the configuration can be made compact.

Preferably in the defect inspection device of the invention, light-intercepting unit for intercepting an optical path of specular reflected light is provided on the optical path of light from the specimen to the light-receiving section, thereby enabling dark field observation.

In this case, since dark field observation is made possible by providing light-intercepting unit for intercepting the optical path of specular reflected light, dark field observation can be performed with a simple configuration.

Preferably in the defect inspection device of the invention, the illumination section is configured in a line shape arranged parallel to the specimen; the illumination section and the light-receiving section rotate around a rotational axis that includes an intersection point between their optical axes and the surface of the specimen, and is parallel to the longitudinal direction of the illumination section.

In this case, since the illumination section and the light-receiving section rotate around a rotational axis that includes an intersection point between their optical axes and the surface of the specimen and is parallel to the longitudinal direction of the illumination section, even if the illumination section and the light-receiving section are rotated, the illumination light is illuminated in substantially the same line shape, making it unnecessary to adjust the inspection position and enabling the inspection efficiency to be increased.

Preferably in the defect inspection device of the invention, the light-receiving section receives diffracted light from the specimen. Moreover, the diffracted light is preferably diffracted in the same direction as the incident direction of the illumination light.

In this case, inspection can be performed using diffracted light over a wide angle range. In particular, when the diffracted light is diffracted in the same direction as the incident angle of the illumination light, according to Bragg's law, the received light is low-noise diffracted light that is not dependent on changes in the thickness of the specimen and the like, making image processing easier and increasing the inspection precision.

Preferably in the defect inspection device of the invention, the illumination section is arranged as a plurality of illumination sections that illuminate the specimen at mutually different incident angles, the incident direction of illumination light from at least one of the plurality of illumination sections being different to the light-receiving direction of the light-receiving section.

In this case, illumination light from at least one of the plurality of illumination sections can be emitted in a direction that is different from the direction that light emitted from the specimen is received in by the light-receiving section. Therefore, illumination light from at least one of the plurality of illumination sections can be using in forming illumination light suitable for dark field observation and the like.

Preferably, the defect inspection device of the invention further includes illumination control unit that controls at least a flash duty ratio of illumination light from the illumination section, and image-capture control unit that controls an exposure time of the light-receiving section.

In this case, since the illumination control unit can control the quantity of light by controlling the flash time of the illumination light from the illumination section, and the image-capture control unit can control the amount of exposure of the light-receiving section by controlling the exposure time of the light-receiving section, the luminance of the inspection image can be easily varied. Furthermore, since the illumination control unit and the image-capture control unit both control time, both their controls can be coordinated by simple control unit.

A substrate manufacturing system of the invention includes a substrate manufacturing device that manufactures a substrate, and the abovementioned defect inspection device that performs defect inspection with the substrate in a manufacturing step as the specimen.

According to this invention, it is possible to realize a substrate manufacturing system that achieves similar effects to the defect inspection device of the invention.

Incidentally, the preferred embodiments of the defect inspection device of the invention described above can be combined as appropriate. Furthermore, any of them can be used in the substrate manufacturing system of the invention.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

While the above explanation assumes that the image-capturing elements of the light-receiving element 401 are line sensors, if an image of the inspection range can be captured and subjected to photoelectric conversion, two-dimensional sensors can be used.

Furthermore, while the above explanation of the defect inspection device describes an example where the illumination section and the light-receiving section are held together at a constant angle, they need not be provided together, it being necessary only that such a positional relationship can be maintained during inspection. For example, they can be supported by independently movable holding sections, and their movement controlled while maintaining a constant angle between them. Also, the constant angle can be adjusted to a different constant angle for each inspection.

What is claimed is:

1. A defect inspection device comprising:
an illumination section that irradiates a specimen with a band of illumination light having a variable incident angle; and
a light-receiving section including a line sensor which receives light from the specimen irradiated with illumination light from the illumination section with a variable detection angle,
wherein the specimen has a regular pattern on a surface at a side facing the light-receiving section,
wherein the illumination section and the light-receiving section rotate around a rotational axis that includes an intersection point at which an optical axis of the illumination section, an optical axis of the light-receiving section, and a surface at the light-receiving section side of the specimen intersect, and
wherein the light-receiving section receives diffracted light emitted in substantially a same direction as a direction of incidence of the illumination light from the illumination section.

2. The defect inspection device according to claim 1, wherein the rotational axis is parallel to a longitudinal direction of the band of illumination light which has been irradiated on the surface of the specimen by the illumination section.

3. The defect inspection device according to claim 1, wherein the optical axis of the illumination section and the optical axis of the light-receiving section are partially coaxial.

4. The defect inspection device according to claim 1, wherein, by arranging an optical path splitting unit on an optical path of light emitted from the illumination section, irradiated to the specimen, and received from the specimen at the light-receiving section, the optical axes of the light-receiving section and the illumination section are made partially coaxial.

5. The defect inspection device according to claim 1, wherein the illumination section and the light-receiving section are rotatable together.

6. The defect inspection device according to claim 1, wherein a reflecting member is provided on an optical path of light emitted from the illumination section, irradiated to the specimen, and received from the specimen at the light-receiving section, whereby the optical path is folded.

7. The defect inspection device according to claim 1, wherein a light-intercepting unit for intercepting an optical path of specular reflected light is provided on an optical path of light from the specimen to the light-receiving section, thereby enabling dark field observation.

8. The defect inspection device according to claim 1, wherein the diffracted light is diffracted in the same direction as the incident direction of the illumination light.

9. The defect inspection device according to claim 1, wherein the illumination section is arranged as a plurality of illumination sections that illuminate the specimen at mutually different incident angles, wherein the incident direction of illumination light from at least one of the plurality of illumination sections is different from a light-receiving direction of the light-receiving section.

10. The defect inspection device according to claim 1, further comprising:
   an illumination control unit that controls at least a flash duty ratio of illumination light from the illumination section; and
   an image-capture control unit that controls an exposure time of the light-receiving section.

11. A substrate manufacturing system comprising:
   a substrate manufacturing device that manufactures a substrate; and
   the defect inspection device according to claim 1 that performs defect inspection with the substrate in a manufacturing step as the specimen.

12. A defect inspection device, comprising:
   an illumination section that irradiates a specimen with a band of illumination light having a variable incident angle; and
   a light-receiving section including a line sensor which receives light from the specimen irradiated with illumination light from the illumination section with a variable detection angle,
   wherein the specimen has a regular pattern on a surface at a side facing the light-receiving section,
   wherein an angle between an optical axis of the illumination section and an optical axis of the light-receiving section is a minute angle, and the illumination section and the light receiving section are arranged to rotate as a unit in a state in which the minute angle is maintained around a rotational axis that includes an intersection point at which the optical axis of the illumination section, the optical axis of the light-receiving section, and a surface at the light-receiving section side of the specimen intersect, and
   wherein the light-receiving section receives the light emitted in a direction having the minute angle with respect to a direction of incidence of the illumination light from the illumination section.

* * * * *